US008110560B2

(12) United States Patent
Singh et al.

(10) Patent No.: US 8,110,560 B2
(45) Date of Patent: Feb. 7, 2012

(54) **SPINAL MUSCULAR ATROPHY (SMA) TREATMENT VIA TARGETING OF *SMN2* SPLICE SITE INHIBITORY SEQUENCES**

(75) Inventors: Ravindra N. Singh, Shrewsbury, MA (US); Natalia N. Singh, Shrewsbury, MA (US); Nirmal K. Singh, Temple, TX (US); Elliot J. Androphy, Natick, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 12/545,536

(22) Filed: Aug. 21, 2009

(65) Prior Publication Data

US 2010/0087511 A1 Apr. 8, 2010

Related U.S. Application Data

(62) Division of application No. 11/295,725, filed on Dec. 5, 2005, now Pat. No. 7,838,657.

(60) Provisional application No. 60/633,325, filed on Dec. 3, 2004.

(51) Int. Cl.
*A61K 48/00* (2006.01)
*C07H 21/04* (2006.01)
*C07H 21/02* (2006.01)

(52) U.S. Cl. ... 514/44; 536/23.1; 536/24.31; 536/24.33; 536/24.5

(58) Field of Classification Search ......................... None
See application file for complete search history.

(56) References Cited

U.S. PATENT DOCUMENTS

| | | | |
|---|---|---|---|
| 5,176,996 | A | 1/1993 | Hogan et al. |
| 5,256,775 | A | 10/1993 | Froehler |
| 5,294,564 | A | 3/1994 | Karapiperis et al. |
| 6,376,508 | B1 | 4/2002 | Li et al. |
| 6,753,423 | B1 | 6/2004 | Cook et al. |
| 6,770,633 | B1 | 8/2004 | Robbins et al. |
| 6,962,906 | B2 | 11/2005 | Efimov et al. |
| 2007/0299021 | A1* | 12/2007 | Dunckley et al. ............... 514/44 |

FOREIGN PATENT DOCUMENTS

| | | |
|---|---|---|
| WO | 01/09311 A2 | 2/2001 |
| WO | 2007/002390 A2 | 1/2007 |

OTHER PUBLICATIONS

Batrakova, Elena V. et al., "Mechanism of Pluronic Effect on P-Glycoprotein Efflux System in Blood-Brain Barrier: Contributions of Energy Depletion and Membrane Fluidization," The Journal of Pharmacology and Experimental Therapeutics, vol. 299(2):483-493 (2001).
Brichta, L et al., "Valproic acid increases the SMN2 protein level: a well-known drug as a potential therapy for spinal muscular atrophy," Human Molecular Genetics, vol. 12(19):2481-2489 (2003).
Crooke, S.T., "Antisense strategies," Curr. Mol. Med., vol. 4(5):465-487 (2004).
Dokka, Sujatha et al., "Novel non-endocytic delivery of antisense oligonucleotides," Advanced Drug Delivery Reviews, vol. 44:35-49 (2000).
Efimov, Vladimir A. et al., "Phosphono Peptide Nucleic Acids with a Constrained Hydroxyproline-Based Backbone," Nucleosides, Nucleotides & Nucleic Acids, vol. 22(5-8):593-599 (2003).
Forte, A. et al., "Small Interfering RNAs and Antisense Oligonucleotides for Treatment of Neurological Diseases," Current Drug Targets, vol. 6:21-29 (2005).
Heasman, Janet, "Morpholino Oligos: Making Sense of Antisense?" Developmental Biology, vol. 243:209-214 (2002).
Hofmann, Yvonne et al., "Htra2-b1 stimulates an exonic splicing enhancer and can restore full-length SMN expression to survival motor neuron 2 (SMN2)," PNAS, vol. 97(17):9618-9623 (2000).
Hua, Yimin et al., "Enhancement of SMN2 Exon 7 Inclusion by Antisense Oligonucleotides Targeting the Exon," PLoS Biology, vol. 5(4):e73 (2007).
Ittig, Damian et al., "Nuclear antisense effects in cyclophilin A pre-mRNA splicing by oligonucleotides: a comparison of tricyclo-DNA with LNA," Nucleic Acids Research, vol. 32(1):346-353 (2004).
Jaeger, Laura B. et al., "Transport of Antisense Across the Blood-Brain Barrier," Methods in Molecular Medicine, vol. 106: Antisense Therapeutics, Second Edition, I. Phillips (Ed.) Humana Press, Inc. Totowa, N.J., Chpt. 12:237-251 (2005).
Kole, Ryszard et al., "RNA modulation, repair and remodeling by splice switching oligonucleotides," Acta Biochimica Polonica, vol. 51(2):373-378 (2004).
Kurreck, Jens, "Antisense and RNA interference approaches to target validation in pain research," Current Opinion in Drug Discovery & Development, vol. 7(2):179-187 (2004).
Lim, Sharlene R. et al., "Modulation of Survival Motor Neuron Pre-mRNA Splicing by Inhibition of Alternative 3' Splice Site Pairing," The Journal of Biological Chemistry, vol. 276(48):45476-45483 (2001).
Lorson, Christian L. et al., "A single nucleotide in the SMN gene regulates splicing and is responsible for spinal muscular atrophy," Proc. Natl. Acad. Sci. USA, vol. 96:6307-6311 (1999).
Lu, Qi Long et al., "Systemic delivery of antisense oligoribonucleotide restores dystrophin expression in body-wide skeletal muscles," PNAS, vol. 102(1):198-203 (2005).
Madocsai, Csilla et al., "Correction of SMN2 Pre-mRNA Splicing by Antisense U7 Small Nuclear RNAs," Molecular Therapy, vol. 12(6):1013-1022 (2005).

(Continued)

*Primary Examiner* — Amy Bowman
(74) *Attorney, Agent, or Firm* — Nelson Mullins Riley & Scarborough LLP; Debra J. Milasincic, Esq.; Megan E. Williams

(57) ABSTRACT

The present invention is directed to methods and compositions capable of blocking the inhibitory effect of a newly-identified intronic inhibitory sequence element, named ISS-N1 (for "intronic splicing silencer"), located in the SMN2 gene. The compositions and methods of the instant invention include oligonucleotide reagents (e.g., oligoribonucleotides) that effectively target the SMN2 ISS-N1 site in the SMN2 pre-mRNA, thereby modulating the splicing of SMN2 pre-mRNA to include exon 7 in the processed transcript. The ISS-N1 blocking agents of the invention cause elevated expression of SMN protein, thus compensating for the loss of SMN protein expression commonly observed in subjects with spinal muscular atrophy (SMA).

43 Claims, 16 Drawing Sheets

OTHER PUBLICATIONS

Miyajima, Hiroshi et al., "Identification of a Cis-acting Element for the Regulation of SMN Exon 7 Splicing," The Journal of Biological Chemistry, vol. 277(26):23271-23277 (2002).

Miyaso, Hidenobu et al., "An Intronic Splicing Enhancer Element in Survival Motor Neuron (SMN) Pre-mRNA," The Journal of Biological Chemistry, vol. 278(18):15825-15831 (2003).

Rebuffat, Alexandre G. et al., "Gene delivery by a steroid-peptide nucleic acid conjugate," FASEB J., vol. 19 (11):1426-1428 (2002).

Sazani, Peter et al., "Therapeutic potential of antisense oligonucleotides as modulators of alternative splicing," The Journal of Clinical Investigation, vol. 112(4):481-486 (2003).

Singh, Natalia N. et al., "In vivo selection reveals combinatorial controls that define a critical exon in the spinal muscular atrophy genes," RNA, vol. 10:1291-1305 (2004).

Singh, N.N., et al., "An extended inhibitory context causes skipping of exon 7 of SMN2 in spinal muscular atrophy," Biochem. Biophys. Res. Comm., vol. 315(2):381-388 (2004).

Singh, Nirmal K. et al., "Splicing of a Critical Exon of Human Survival Motor Neuron Is Regulated by a Unique Silencer Element Located in the Last Neuron," Molecular and Cellular Biology, vol. 26(4):1333-1346 (2006).

Skordis, Leigh A. et al., "Bifunctional antisense oligonucleotides provide a trans-acting splicing enhancer that stimulates SMN2 gene expression in patient fibroblasts," PNAS, vol. 100(7):4114-4119 (2003).

Veldink, J.H. et al., "SMN genotypes producing less SMN protein increase susceptibility to and severity of sporadic ALS," Neurology, vol. 65(6):820-825 (2005).

Vinogradov, Serguei V. et al., "Nanogels for Oligonucleotide Delivery to the Brain," Bioconjugate Chem., vol. 15:50-60 (2004).

Wahlestedt, Claes et al., "Potent and nontoxic antisense oligonucleotides containing locked nucleic acids," PNAS, vol. 97(10):5633-5638 (2000).

International Search Report for Application No. PCT/US06/24469, dated Sep. 13, 2007.

* cited by examiner

A

| | 10 | ISS-N1 20 | | 30 | | | Lanes in 40 Panel B | |
|---|---|---|---|---|---|---|---|---|
| SMN2 | CCAGC | AUUAU | GAAAG | UGAAU | CUUAC | UUUUG | UAAAA | |
| N1A10-14 | ----- | AUUAU | GAAAG | UGAAU | CUUAC | UUUUG | UAAAA | 3 SEQ ID NO: 72 |
| N1A15-19 | CCAGC | ----- | GAAAG | UGAAU | CUUAC | UUUUG | UAAAA | 4 SEQ ID NO: 73 |
| N1A20-24 | CCAGC | AUUAU | ----- | UGAAU | CUUAC | UUUUG | UAAAA | 5 SEQ ID NO: 74 |
| N1A25-29 | CCAGC | AUUAU | GAAAG | ----- | CUUAC | UUUUG | UAAAA | 6 SEQ ID NO: 75 |
| N1A30-34 | CCAGC | AUUAU | GAAAG | UGAAU | ----- | UUUUG | UAAAA | 7 SEQ ID NO: 76 |
| N1A10-19 | ----- | ----- | GAAAG | UGAAU | CUUAC | UUUUG | UAAAA | 8 SEQ ID NO: 77 |
| N1A15-24 | CCAGC | ----- | ----- | UGAAU | CUUAC | UUUUG | UAAAA | 9 SEQ ID NO: 78 |
| N1A20-29 | CCAGC | AUUAU | ----- | ----- | CUUAC | UUUUG | UAAAA | 10 SEQ ID NO: 79 |
| N1A25-34 | CCAGC | AUUAU | GAAAG | ----- | ----- | UUUUG | UAAAA | 11 SEQ ID NO: 80 |
| N1A10-24 | ----- | ----- | ----- | UGAAU | CUUAC | UUUUG | UAAAA | 12 SEQ ID NO: 81 |
| N1A15-29 | CCAGC | ----- | ----- | ----- | CUUAC | UUUUG | UAAAA | 13 SEQ ID NO: 82 |
| N1A20-34 | CCAGC | AUUAU | ----- | ----- | ----- | UUUUG | UAAAA | 14 SEQ ID NO: 83 |
| N1A15-34 | CCAGC | ----- | ----- | ----- | ----- | UUUUG | UAAAA | 15 SEQ ID NO: 84 |
| N1A26-30 | CCAGC | AUUAU | GAAAG | UGAAU | ----- | UUUUG | UAAAA | 16 SEQ ID NO: 85 |
| N1A10-29 | ----- | ----- | ----- | ----- | CUUAC | UUUUG | UAAAA | 17 SEQ ID NO: 86 |
| N1A10-34 | ----- | ----- | ----- | ----- | ----- | UUUUG | UAAAA | 18 SEQ ID NO: 87 |

U1 snRNA: GUAAGUCUG (paired with each row above)

INTRON 7 →

SPINAL MUSCULAR ATROPHY (SMA) TREATMENT VIA TARGETING OF *SMN2* SPLICE SITE INHIBITORY SEQUENCES

RELATED APPLICATIONS

This application is a divisional of U.S. patent application Ser. No. 11/295,725 filed Dec. 5, 2005, which claims the benefit of U.S. Ser. No. 60/633,325, entitled "Spinal Muscular Atrophy (SMA) Treatment Via Targeting of SMN2 Splice Site Inhibitory Sequences," filed on Dec. 3, 2004. The entire contents of these applications are hereby incorporated herein by reference.

STATEMENT AS TO FEDERALLY SPONSORED RESEARCH

Funding for the work described herein was at least in part provided by the federal government (N.I.H. grant R01 NS40275). The government may, therefore, have certain rights in the invention.

RELATED INFORMATION

The contents of any patents, patent applications, and references cited throughout this specification are hereby incorporated by reference in their entireties.

BACKGROUND OF THE INVENTION

Alternative splicing increases the coding potential of human genome by producing multiple proteins from a single gene (Black, D. L. 2003. *Annu. Rev. Biochem.* 72:291-336). It is also associated with a growing number of human diseases (Faustino, N. A., and T. A. Cooper. 2003. Genes Dev. 17:419-437; Garcia-Blanco, M. A., et al. 2004. *Nat. Biotechnol.* 22:535-546; Pagani, F., and F. E. Baralle. 2004. *Nat. Rev. Genet.* 5:389-396).

Proximal spinal muscular atrophy (SMA) is the second most common autosomal recessive disorder, and is characterized by the loss of motor neurons in the anterior horn of the spinal cord (Pearn, Lancet 8174, 919-922). Linkage mapping identified the Survival of Motor Neuron (SMN) gene as the genetic locus of SMA (Lefebvre et al., Cell 80, 1-5). In humans, two nearly identical SMN genes (SMN1 and SMN2) exist on chromosome 5q13. Deletions or mutations within SMN1 but not the SMN2 gene cause all forms of proximal SMA (Lefebvre et al., Cell 80, 1-5). SMN1 encodes a ubiquitously expressed 38 kDa SMN protein that is necessary for snRNP assembly, an essential process for cell survival (Wan, L., et al. 2005. *Mol. Cell. Biol.* 25:5543-5551). A nearly identical copy of the gene, SMN2, fails to compensate for the loss of SMN1 because of exon 7 skipping, producing an unstable truncated protein, SMNΔ7 (Lorson, C. L., et al. 1998. *Nat. Genet.* 19:63-66). SMN1 and SMN2 differ by a critical C to T substitution at position 6 of exon 7 (C6U in transcript of SMN2) (Lorson, C. L., et al. 1999. *Proc. Natl. Acad. Sci. USA* 96:6307-6311; Monani, U. R., et al. 1999. *Hum. Mol. Genet.* 8:1177-1183). C6U does not change the coding sequence, but is sufficient to cause exon 7 skipping in SMN1. Two mutually exclusive models have been proposed to explain the inhibitory effect of C6U. According to one model, C6U abrogates an ESE associated with SF2/ASF (Cartegni, L., and A. R. Krainer. 2002. *Nat. Genet.* 30:377-384), whereas another model proposes that C6U creates an ESS associated with hnRNP A1 (Kashima, T., and J. L. Manley. 2003. *Nat. Genet.* 34:460-463).

Exon 7 is known to have a weak 3' ss (Lim, S. R., and K. J. Hertel. 2001. *J. Biol. Chem.* 276:45476-45483), likely due to its suboptimal polypyrimidine tract. An improved polypyrimidine tract promoted inclusion of exon 7 in SMN2 (Lorson, C. L., and E. J. Androphy. 2000. *Hum. Mol. Genet.* 9:259-265), indicating that the negative interactions at C6U and the positive interactions at the polypyrimidine tract were mutually exclusive. Several splicing factors have been implicated in modulation of SMN exon 7 splicing. Most studied among them has been the SR-like protein, Tra2-β1, that binds to a purine-rich ESE in the middle of exon 7 (Hofmann, Y., et al. 2000. *Proc. Natl. Acad. Sci. USA* 97:9618-23). Elevated expression of Tra2-β1 (ibid.) or its associated proteins, hnRNP G (Hofmann, Y., and B. Wirth. 2002. *Hum. Mol. Genet.* 11:2037-2049) and Srp30c (Young, P. J., et al. 2002. *Hum. Mol. Genet.* 11:577-587), has been shown to promote exon 7 inclusion in SMN2. A recent report in which increased expression of STAR (signal transduction and activation of RNA) family of proteins promoted exclusion of exon 7 indicated that tissue-specific regulation might occur (Stoss, O., et al. 2004. *Mol. Cell. Neurosci.* 27:8-21). Proteins interacting with intronic sequences could also affect regulation of exon 7 splicing. Consistently, cis-elements present in intron 6 and intron 7 have been shown to modulate exon 7 splicing (Miyajima, H., et al. 2002. *J. Biol. Chem.* 277:23271-23277; Miyaso, H., et al. 2003. *J. Biol. Chem.* 278:15825-15831). These results have highlighted the complexity of pre-mRNA splicing, in which exon 7 is defined by a network of interactions involving several proteins.

The 54-nucleotide-long exon 7 of human SMN genes contains ~65% of A+U residues. Hence, exon 7 fits into the typical definition of a cassette exon that generally contains a low percentage of G+C residues (Clark, F., and T. A. Thanaraj. 2002. *Hum. Mol. Genet.* 11:451-64). In addition to the exon 7 sequence, intronic sequences located immediately upstream of the 3' ss or downstream of the 5' splice site (5' ss) of SMN2 exon 7 have been demonstrated as functionally important in splicing (Miriami, E., et al. 2003. *Nucleic Acids Res.* 31:1974-1983; Zhang, X. H., and L. A. Chasin. 2004. *Genes Dev.* 18:1241-1250). These sequences are highly diverse and can be broadly categorized into G+C-rich and A+U-rich regions that constitute distinct pentamer motifs (Zhang, X. H., et al. 2005. *Genome Res.* 15:768-779). Intron 7 sequence downstream of the 5' ss is rich in A and U residues, but lacks characteristic pentamer motifs.

SMN function correlates with its ability to self-associate (Lorson et al., Nat. Genet. 19, 63-66). SMN also performs a housekeeping role by helping regenerate the spliceosome through a multi-component SMN complex (Meister et al., Trends Cell Biol. 12, 472-478; Gubitz et al., Exp. Cell. Res. 296, 51-56). Many recent reviews highlight the functional role of SMN with direct implications to SMA (Ogino and Wilson, Expert. Rev. Mol. Diagn. 4, 15-29; Iannaccone et al., Curr. Neurol. Neurosci. Rep. 4, 74-80). The defects caused by the lack of SMN1 can be partially compensated by high copy number of SMN2, which produces low levels of the full-length protein (Monani et al., Hum. Mol. Genet. 9, 2451-2457; Stoilov et al., DNA Cell Biol. 21, 803-818). Most SMA patients have an SMN2 gene, thus, therapies that improve the levels of exon 7 inclusion in SMN2 are likely to be effective.

Antisense technology, used mostly for RNA downregulation, recently has been adapted to alter the splicing process (Kole et al., *Acta Biochim Pol.* (2004) 51, 373-8). Techniques that trick the splicing machinery to alter splicing of SMN2 pre-mRNAs are likely to have high therapeutic value.

SUMMARY OF THE INVENTION

The present invention is based, at least in part, on the discovery that antisense targeting, displacement and/or disruption of an intronic sequence in the SMN2 gene can enhance production of full-length SMN2 transcripts (transcripts containing exon 7) during splicing. In particular, the present inventors have identified a novel intronic inhibitory sequence element, named ISS-N1 (for "intronic splicing silencer"), in the SMN2 gene as a desirable therapeutic target. Accordingly, the invention is directed to effective use of ISS-N1 blocking agents, in particular, blocking oligonucleotide reagents (e.g., modified antisense oligoribonucleotides) to inhibit this intronic splice-inhibitory sequence. Treatment of cells derived from SMA patients with the oligonucleotide reagent compositions of the instant invention effectively restored the production of the full-length SMN protein. These results demonstrate for the first time the therapeutic value of oligonucleotide reagent inhibition of an SMN2 splice site inhibitory domain, which in exemplary embodiments is achieved through specific inhibition of the ISS-N1 domain using an anti-ISS-N1 (anti-N1) oligonucleotide.

The present invention therefore is directed to compositions capable of blocking the inhibitory effects of the newly-discovered SMN2 intronic splice silencing domain, ISS-N1. Agents capable of blocking the splice-inhibitory effect of this domain have high value as SMA therapeutics. Featured agents capable of blocking the splice-inhibitory effect of the SMN2 ISS-N1 domain include, but are not limited to, e.g., agents that disrupt the interaction of an ISS-N1-interacting protein with the ISS-N1 sequence, agents that sequester an ISS-N1 interacting protein, agents that disrupt the structure of the ISS-N1 domain and/or surrounding regions (including, e.g., the U1 snRNP binding site within the SMN2 pre-mRNA that lies proximal to the ISS-N1 sequence domain).

In exemplary embodiments, the instant invention is directed to oligonucleotide reagents (e.g., modified antisense oligoribonucleotides) that block the effect on pre-mRNA splicing of the SMN2 ISS-N1 sequence via direct interaction and/or hybridization with the ISS-N1 sequence. Such RNA-complementary oligonucleotide reagents may be modified by art-recognized means to improve their in vivo stabilities and/or bioaccessibility. The instant invention also is directed to methods for identifying ISS-N1-interacting proteins, as such methods are enabled by discovery and characterization of the ISS-N1 sequence.

In one aspect, the instant invention is directed to an isolated oligonucleotide reagent (e.g., an oligoribonucleotide) comprising a nucleotide sequence which is complementary to an ISS-N1 sequence.

In another aspect, the instant invention is directed to an isolated oligonucleotide reagent (e.g., an oligoribonucleotide) which is complementary to the sequence 5'-CCAGCAUUAUGAAAG-3' (SEQ ID NO: 3).

In an additional aspect, the instant invention is directed to an isolated oligonucleotide reagent (e.g., an oligoribonucleotide) which is complementary to the sequence 5'-CCAGCAUU-3' (SEQ ID NO: 1).

In a further aspect, the instant invention is directed to an isolated oligonucleotide reagent (e.g., an oligoribonucleotide) which is complementary to the sequence 5'-CCAGCNNNNNGAAAG-3' (SEQ ID NO: 5).

In another aspect, the instant invention is directed to an isolated oligonucleotide reagent (e.g., an oligoribonucleotide) which is greater than 80% complementary to the sequence 5'-CCAGCAUUAUGAAAG-3' (SEQ ID NO: 3)

In an additional aspect, the instant invention is directed to an isolated oligonucleotide sequence comprising the sequence 5'-CUUUCAUAAUGCUGG-3' (SEQ ID NO: 4).

In another aspect, the instant invention is directed to an isolated oligonucleotide sequence comprising the sequence 5'-AAUGCUGG-3' (SEQ ID NO: 2).

In a further aspect, the instant invention is directed to an isolated oligonucleotide sequence comprising the sequence 5'-CUUUCNNNNNGCUGG-3' (SEQ ID NO: 6).

In another aspect, the instant invention is directed to an isolated oligonucleotide reagent comprising a sequence greater than 80% identical to the sequence 5'-CUUUCAUAAUGCUGG-3' (SEQ ID NO: 4).

In one embodiment, the oligonucleotide is modified by the substitution of at least one nucleotide with a modified nucleotide, such that in vivo stability is enhanced as compared to a corresponding unmodified oligonucleotide. In a related embodiment, the modified nucleotide is a sugar-modified nucleotide. In another embodiment, the modified nucleotide is a nucleobase-modified nucleotide.

In an additional embodiment, the modified nucleotide is a 2'-deoxy ribonucleotide. In certain embodiments, the 2'-deoxy ribonucleotide is 2'-deoxy adenosine or 2'-deoxy guanosine. In another embodiment, the modified nucleotide is a 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) ribonucleotide. In an additional embodiment, the modified nucleotide is selected from the group consisting of a 2'-fluoro, 2'-amino and 2'-thio modified ribonucleotide. In a further embodiment, the modified nucleotide is selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine. In an additional embodiment, the modified nucleotide is selected from the group consisting of 5-bromo-uridine, 5-iodo-uridine, 5-methyl-cytidine, ribothymidine, 2-aminopurine, 5-fluoro-cytidine, and 5-fluorouridine, 2,6-diaminopurine, 4-thio-uridine, and 5-amino-allyl-uridine.

In a further embodiment, the modified nucleotide is a backbone-modified nucleotide. In one embodiment, the backbone-modified nucleotide contains a phosphorothioate group. In another embodiment, the modified nucleotide is a locked nucleic acid (LNA).

Another embodiment is directed to a composition comprising an oligonucleotide of the invention. In certain embodiments, the composition further comprises a pharmaceutical carrier.

An additional embodiment of the invention is directed to a method of enhancing the level of exon 7-containing SMN2 mRNA relative to exon-deleted SMN2 mRNA in a cell or cell extract, comprising contacting the cell or cell extract with an oligonucleotide (e.g., an oligoribonucleotide) of the invention, such that the level of exon 7-containing SMN2 mRNA relative to exon-deleted SMN2 mRNA in the cell or cell extract is enhanced. In one embodiment, the cell or cell extract is a spinal muscular atrophy (SMA) patient-derived neuronal cell, muscle cell or fibroblast, or extract thereof. In certain embodiments, the cell or cell extract is selected from the group consisting of an embryonic stem cell, an embryonic stem cell extract, a neuronal stem cell and a neuronal stem cell extract.

A related embodiment of the invention is directed to a method of enhancing the level of exon 7-containing SMN2 mRNA relative to exon-deleted SMN2 mRNA in an organism, comprising administering to the organism an oligonucleotide of the invention (e.g., an oligoribonucleotide), such that the level of exon 7-containing SMN2 mRNA relative to exon-deleted SMN2 mRNA in the organism is enhanced. In one embodiment, the organism is a mammal. In another embodiment, the organism is a human. In certain embodiments, the human has spinal muscular atrophy (SMA).

Another embodiment of the invention is directed to a method of treating spinal muscular atrophy (SMA) in a patient, comprising administering to the patient an oligonucleotide of the invention (e.g., an oligoribonucleotide) in a dose effective to enhance the level of exon 7-containing SMN2 mRNA relative to exon-deleted SMN2 mRNA in cells of the patient, such that SMA in the patient is treated.

A further embodiment is directed to a method for inhibiting an SMN2 pre-mRNA intronic splicing silencer site in a cell or cell extract comprising contacting the cell with an oligonucleotide of the invention (e.g., an oligoribonucleotide), such that the SMN2 intronic splicing silencer site is inhibited. In a related embodiment, the instant invention is directed to a method for inhibiting an SMN2 pre-mRNA intronic splicing silencer site in an organism comprising administering to the organism an oligonucleotide of the invention, such that the SMN2 intronic splicing silencer site is inhibited. Another embodiment is directed to a method for inhibiting an SMN2 pre-mRNA intronic splicing silencer site in a subject with SMA comprising administering to the subject an oligonucleotide of the invention (e.g., an oligoribonucleotide), such that the SMN2 intronic splicing silencer site is inhibited.

An additional aspect of the invention is directed to a method for identifying a protein that interacts with the ISS-N1 sequence set forth as SEQ ID NO: 1, comprising contacting a cell or cell extract with the ISS-N1 sequence under conditions sufficient for the sequence to interact with a protein in the cell or cell extract; and isolating the ISS-N1 sequence and interacting protein, such that the protein that interacts with the ISS-N1 sequence is identified. In one embodiment, the method further comprises UV-crosslinking the ISS-N1 sequence to the interacting protein. In an additional embodiment, the cell or cell extract is of mammalian origin. In certain embodiments, the cell or cell extract is of human origin.

Another aspect of the invention is directed to a method of enhancing the level of exon 7-containing SMN2 mRNA relative to exon-deleted SMN2 mRNA in a cell or cell extract, comprising contacting the cell or cell extract with an ISS-N1 blocking agent, such that the level of exon 7-containing SMN2 mRNA relative to exon-deleted SMN2 mRNA in the cell or cell extract is enhanced. A related aspect of the invention is directed to a method of enhancing the level of exon 7-containing SMN2 mRNA relative to exon-deleted SMN2 mRNA in an organism, comprising contacting the organism with an ISS-N1 blocking agent, such that the level of exon 7-containing SMN2 mRNA relative to exon-deleted SMN2 mRNA in the organism is enhanced.

In one embodiment, the ISS-N1 blocking agent is selected from the group consisting of a small molecule, a peptide, a polynucleotide, an antibody or biologically active portion thereof, a peptidomimetic, and a non-peptide oligomer. In an additional embodiment, the ISS-N1 blocking agent is a small molecule.

In another aspect, the invention is directed to a method for inhibiting the splicing of an exon, comprising insertion of an ISS-N1 sequence at a site within 40 nucleotides of the 5' splice site of the exon.

In an additional aspect, the invention is directed to a method of treating amyotrophic lateral sclerosis (ALS) in a patient, comprising administering to the patient the oligonucleotide of any of claims 1-21 in a dose effective to enhance the level of exon 7-containing SMN2 mRNA relative to exon-deleted SMN2 mRNA in cells of the patient.

In an additional embodiment, the oligonucleotide reagent of the invention is a ribozyme.

Other features and advantages of the invention will be apparent from the following detailed description and claims.

BRIEF DESCRIPTION OF THE DRAWINGS

FIG. 2A depicts positions of the mutations (SEQ ID NOS 68-70).

FIG. 3A schematically depicts the eight-nucleotide-long sequence (SEQ ID NO: 71) stretch in which six nucleotide positions (marked as "N") were randomized to generate the initial pool of mutants tested for alteration of SMN2 splicing. Sequences of a randomly-picked eleven clones (from the initial pool) are shown.

FIG. 4A depicts intronic sequences of SMN2 deletion mutants (SEQ ID NOS 72-87, respectively in order of appearance). Nucleotide numbering starts from the beginning of intron 7, and deletions are shown as dashed lines. The ISS-N1 site is shaded. Nucleotides involved in base pairing with U1 snRNA are shown in bold and highlighted. Numbers in mutants' names represent the span of positions deleted. FIG. 4B shows the in vivo splicing pattern of the SMN2 deletion mutants shown in panel A. The upper band corresponds to fully-spliced product that includes exon 7; the lower band corresponds to exon 7-skipped product. The percent of exon 7 skipping was calculated from the total value of exon-7-included and exon-7-skipped products. Abbreviations E6, E7, and E8 stand for exon 6, exon 7, and exon 8, respectively. FIG. 4C shows the in vivo splicing pattern of SMN2ΔISS-N1 (ISS-N1-deleted mutant) in different cell lines. Notably, SMN2ΔISS-N1 was the same construct as the N1Δ10-24 mutant in FIG. 4A. Cell lines used were Neuro-2a (mouse brain neuroblastoma, lanes 1-3), NSC34 (mouse motor neuron-like, lanes 4-6), SK-N-SH (human neuroblastoma, lanes 7-9), P-19 (mouse embryonal teratocarcinoma, lanes 10-12), HEK293 (human embryonal kidney cells, lanes 13-15). Spliced products were the same as indicated in FIG. 4B.

FIG. 5A shows an alignment of the first 42 nucleotides of human and mouse intron 7, including the ISS-N1 region. Sequence numbering starts from the beginning of intron 7, with the ISS-N1 sequence shaded. Nucleotides involved in base pairing with U1 snRNA are shown in bold and highlighted. In the top two lines, homologous positions between human and mouse sequences are shaded in black. In the bottom ten lines, intronic sequences of SMN2 mutants (SMN2/MS1 through SMN2/MS10) are shown with mouse nucleotides written in lower-case letters and highlighted in black (SEQ ID NOS 88-99, respectively in order of appearance).

FIG. 7A depicts the sequence of the anti-N1 oligonucleotide (SEQ ID NO: 39) and its annealing site within intron 7 of the SMN2 pre-mRNA (SEQ ID NO: 103). FIG. 7B shows that the anti-N1 oligonucleotide mediated restoration of exon 7 inclusion in SMN2 when transiently transfected to cells. The prominent antisense effect was observed even at the lowest concentration of the anti-N1 oligonucleotide (25 nM). FIG. 7C shows that the anti-N1 oligonucleotide had no effect on splicing of mutants that have a deleted or mutated ISS-N1 site. In ΔN1S and ΔN1L mutants, ISS-N1 was completely deleted, while in Mut-N1, the ISS-N1 domain is mutated. Lack of improvement of exon 7 inclusion in the presence of anti-N1 oligonucleotide confirmed that the effect of anti-N1 oligonucleotide was sequence-specific.

FIG. 8A (SEQ ID NO: 104) depicts a diagrammatic representation of intron 7 regions targeted by antisense oligonucleotides Anti-N1, Anti-N1+10, Anti-N1+20 and Anti-N1+30. Sequence numbering starts from the beginning of intron 7. The ISS-N1 region is highlighted. Of the four oligonucleotides shown, only Anti-N1 fully sequestered ISS-N1. FIG. 8B shows the in vivo splicing pattern of SMN2 minigene in the presence of antisense oligonucleotides. Spliced products are the same as indicated in FIG. 4B. FIG. 8C shows the in vivo splicing pattern of different minigenes in the presence of Anti-N1. In every lane, the upper band represents the exon included, whereas the lower band represents the exon-excluded products. For CFTR, apoA-II, Fas and Casp3, the major bands represent the exon-included products. For Tau and Fas (mut), the major bands represent the exon-excluded products. For detection of spliced products in lanes 1-6, 9 and 10, cells were harvested 40 hours after transfection (for other lanes, refer to Materials and Methods).

FIG. 9A shows the intron 7 sequences of SMN2 and mutants with substitutions in the ISS-N1 region (SEQ ID NOS 72 and 105-107, respectively in order of appearance). Sequence numbering starts from the beginning of intron 7. The ISS-N1 region is highlighted in grey. Nucleotides involved in base pairing with U1 snRNA are shown in bold and highlighted. Note that intronic mutations (highlighted in black) abrogate base pairing between Anti-N1 and ISS-N1. FIG. 9B shows the nucleotide sequence of Anti-N1 (SEQ ID NO: 39) and Anti-I7-25 (SEQ ID NO: 108) oligonucleotides. Differences are highlighted in black. Note that Anti-I7-25 will restore base pairing with ISS-N1 region in mutant SMN2/I7-25. FIG. 9C shows the in vivo splicing pattern of mutants shown in FIG. 9A. Plasmid DNA (0.1 μg) was transfected alone or co-transfected with 50 nM of Anti-N1 or Anti-I7-25 oligonucleotide. Spliced products were the same as indicated in FIG. 4B.

FIG. 10A depicts a diagrammatic representation of several cis-elements involved in regulation of exon 7 splicing (not to the scale). Elements 1G, Tra2-β1 (Tra2-ESE), CT (Conserved Tract) and element 2 represent positive elements (marked as "+"). The ISS-N1 domain is a negative element (marked as "−").

In FIG 11A, the upper panel shows the location of ISS-N1 within SMN2 intron 7 with respect to the 5' ss (SEQ ID NOS 109-113, respectively in order of appearance). The ISS-N1 sequence was inserted at different locations within intron 7 of SMN2SMN2 mutants with 5-nucleotide-long insertions immediately upstream of ISS-N1 (SEQ ID NOS 72 and 114-117, respectively in order of appearance). Nucleotide position and types of insertions are indicated. Sequence numbering starts from the beginning of intron 7. The ISS-N1 sequence is shaded. Nucleotides involved in base pairing with U1 snRNA are shown in bold and highlighted. FIG 11B shows the in vivo splicing pattern of mutants shown in FIG. 11A. Spliced products were the same as indicated in FIG. 4B. FIG. 11C shows the effect of insertion of ISS-N1 in a heterologous context. For insertion of the ISS-N1 sequence, Avr II restriction site was first inserted downstream of exon 6 of Casp3 minigene (SEQ ID NOS 118 and 119). FIG. 11D shows the in vivo splicing pattern of mutants shown in FIG. 11C. The splicing pattern was determined in the absence and presence of antisense oligonucleotide (Anti-ISS-N1/15) that fully sequestered ISS-N1. In the absence of Anti-ISS-N1/15, Casp3ISS-N1 mutant increased exclusion of Casp3 exon 6 (compare lane 3 with 4).

FIG. 12A shows the splicing of endogenous SMN2 after SMA fibroblasts (GM03813) were transfected with 5 nM of oligonucleotides. Total RNA was collected 25 hours after transfection. FIG. 12B demonstrates the specificity of Anti-N1 on the splicing pattern of other exons in SMA fibroblasts (GM03813). The sizes of the expected spliced products are indicated to the left. The same RNA used in FIG. 12A (lanes 2 and 3) was used for this analysis. The 662-bp band in lanes 1 and 2 represents SMN-exon-3-included product, whereas 387-bp band in lanes 3 and 4 represent SMN-exon-5-included product. The 440-bp band in lanes 5 and 6 represents transcripts that exclude exons 2b but include exon 3 of Survivin (Mahotka, C., et al. 1999. *Cancer Res.* 59:6097-6102). The 830 by band in lanes 7 and 8 represents transcripts that include exons 29 and 30 of NF1 (Park, V. M., et al. 1998. *Hum. Genet.* 103:382-385). The 686 by band in lanes 9 and 10 represents transcripts that produce Tra2-β1 spliced variant of Tra2 (Chen, X., et al. 2003. *Cell Biol. Int.* 27:491-496). The 474 by band in lanes 11 and 12 represents Caspase 3 exon 6 included product (Huang, Y., et al. 2001. *Biochem. Biophys. Res. Commun.* 283:762-769).

The 300 by band in lanes 13 and 14 represents Bcl-xL spliced variant of Bcl-x (Mercatante, D. R., et al. 2002. *J. Biol. Chem.* 277:49374-49382). FIG. 12C shows antisense oligonucleotide-mediated (anti-N1-mediated) restoration of SMN protein in patient cells. The antisense effect was verified at the protein level for SMA patient-derived fibroblasts. SMA fibroblasts were transfected with anti-N1 oligonucleotide and cell lysates were prepared 48 and 72 hours post-transfection. As shown in lanes 1 and 4, the level of SMN protein increased as compared to the untransfected cells (lanes 2 and 5). To ensure even protein loading, membranes were stained with Sypro Ruby Protein Blot™ stain (Bio-Rad). In addition, SMN protein levels were compared to alpha-tubulin levels as an internal control (though elevated alpha-tubulin levels have consistently been observed in patient fibroblasts as compared to normal fibroblasts). FIG. 12D also shows the effect of Anti-N1 on the level of SMN protein. Western blots were performed to detect SMN in SMA fibroblasts (GM03813) transfected with 5 nM (lane 1) and 15 nM (lane 3) of Anti-N1. GM03813 cells transfected with control oligonucleotide Scramble20 (lanes 2 and 4), and mock transfected GM03813 cells (lane 5) or AG06814 cells (normal fibroblasts) (lane 6) were used as controls. For detection of SMN, cells were harvested 72 hours after transfection. α-tubulin was used as a loading control.

DETAILED DESCRIPTION OF THE INVENTION

Figure 1:
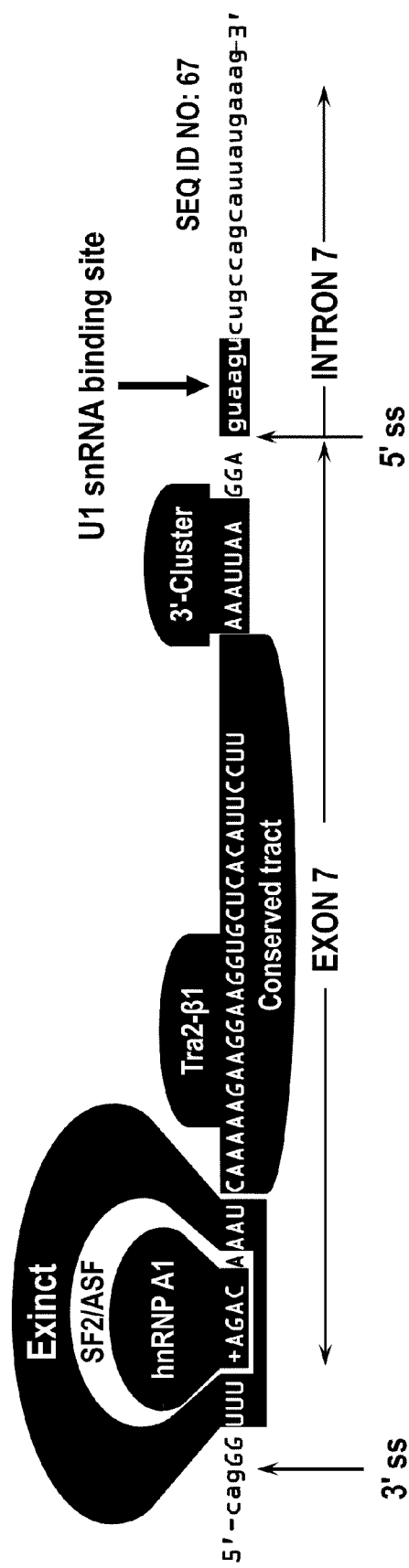
FIG. 1 presents a model of cis-elements that regulate splicing of exon 7 of human SMN, wherein upper-case letters represent exon 7 sequences, lower-case letters represent intronic sequences, and the asterisk (*) represents position 6, where C is replaced by U (C6U) in SMN2 exon 7 (SEQ ID NO: 67). The U1 snRNA binding site that spans the first six nucleotides of intron 7 is also highlighted.
Figure 2:
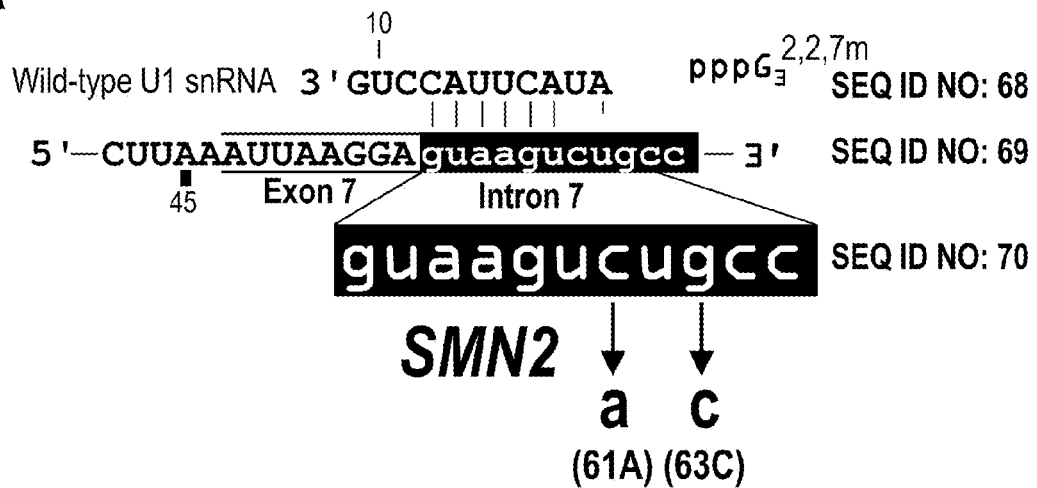
FIGS. 2A and B show the effect on SMN2 splicing of mutations in SMN2 intron 7, some of which restored strong U1 snRNA base-pairing at the 5' splice site (ss) of intron 7, thus identifying the ISS-N1 sequence domain.
FIG. 2B shows the splicing patterns of SMN2 mutants, with Tra2-ESE(−) mutants harboring abrogated Tra2-ESE, performed similarly as in Singh et al., RNA 10, 1291-1305.
Figure 2:
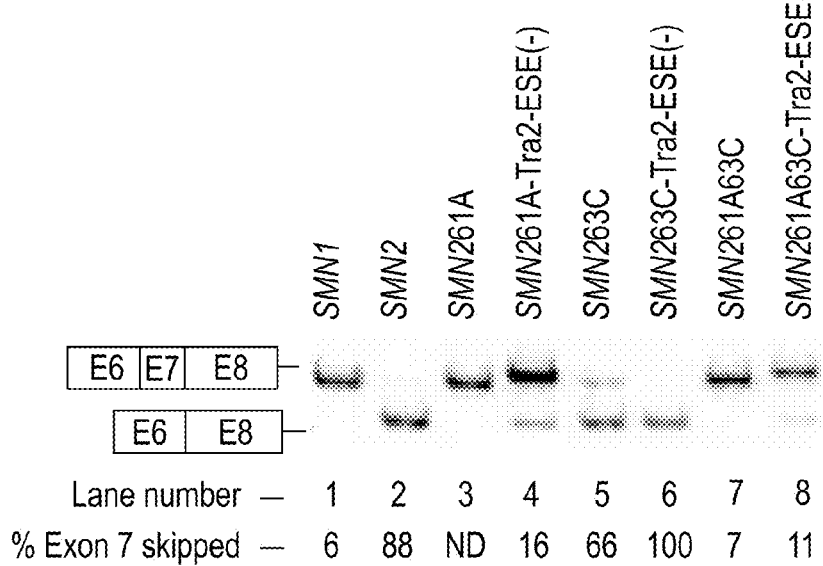

The present invention relates to the discovery that targeting of an intronic sequence in the SMN2 gene can enhance production of full-length SMN2 transcripts (transcripts containing exon 7) during splicing. In particular, the present inventors have identified a novel intronic inhibitory sequence element, named ISS-N1 (for "intronic splicing silencer"), in the SMN2 gene as a valuable therapeutic target. Accordingly, the invention is directed to effective use of blocking compounds, in particular, oligonucleotide reagents (e.g., modified antisense oligoribonucleotides) to inhibit this intronic splice-inhibitory sequence. The ISS-N1 sequence motif was identified to play a dominant role in production of exon 7-deleted SMN2 transcripts. Oligoribonucleotide reagents complementary to ISS-N1 were shown to enhance inclusion of exon 7 during splicing of SMN2 transcript in SMA patient fibroblasts, thus restoring production of full-length SMN2 mRNA transcripts. Consequently, this treatment also restored the production of the full-length SMN protein. Displacement and/or disruption of the ISS-N1 site was also shown to restore inclusion of exon 7 in SMN transcripts; thus, the invention is also directed to therapies that displace and/or disrupt the ISS-N1 sequence. These results demonstrated for the first time the therapeutic value of inhibition of SMN2 splice site inhibitory domains, for example, through specific inhibition of the ISS-N1 domain using an anti-ISS-N1 (anti-N1) oligonucleotide.

The present invention provides compositions for blocking the inhibitory effects of the newly-discovered SMN2 intronic splice silencing domain, ISS-N1. In particular, the invention provides compositions comprising oligonucleotide reagents (e.g., antisense agents or dsDNA cassettes) that block the splice inhibitory effects of the ISS-N1 domain, thereby modulating splicing of the SMN2 pre-mRNA to include exon 7 in processed forms of the transcript. Agents capable of blocking the splicing effect of ISS-N1 have high value as SMA therapeutics. Such agents can also be used in treatment of amyotrophic lateral sclerosis (ALS), another neurological disease characterized by low levels of SMN protein (Veldink, J. H., et al. 2005 *Neurology* 65(6):820-5). The invention therefore provides agents capable of blocking the splice-inhibitory effect of the SMN2 ISS-N1 domain, including but not limited to, e.g., agents that disrupt the interaction of an ISS-N1-interacting protein with the ISS-N1 sequence, agents that sequester an ISS-N1 interacting protein, agents that disrupt the structure of the ISS-N1 domain and/or surrounding regions (including, e.g., the U1 snRNP binding site within the SMN2 pre-mRNA that lies proximal to the ISS-N1 sequence domain).

In exemplary embodiments, the instant invention is directed to oligonucleotide reagents capable of blocking the effect on pre-mRNA splicing of the SMN2 ISS-N1 sequence via direct interaction and/or hybridization. To enhance the therapeutic value of such RNA-complementary oligonucleotides, the invention is further directed to compositions comprising modified forms of such oligonucleotides, e.g., phosphorothioate-, 2'-O-methyl-, etc.-modified oligonucleotides, as such modifications have been recognized in the art as improving the stability of oligonucleotides in vivo. The instant invention also is directed to methods for identifying ISS-N1-interacting proteins, as such methods are enabled by the instant discovery and characterization of the ISS-N1 sequence.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH- group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

As used herein, the term "intronic splicing silencer-N1" or "ISS-N1" refers to the sequence 5'-CCAGCAUUAUGAAAG-3' (SEQ ID NO: 3), or any sequence or variant thereof capable of inhibiting the inclusion of exon 7 during splicing of the SMN2 pre-mRNA. One such effective sequence thereof is 5'-CCAGCAUU-3' (SEQ ID NO: 1). Critical residues that mediate the splice site inhibitory activity of the ISS-N1 sequence can also be represented by the sequence 5'-CCAGCNNNNNGAAAG-3' (SEQ ID NO: 5). Thus, any such sequence that acts to inhibit inclusion of exon 7 during splicing of the SMN2 pre-mRNA can be referred to simply as an "ISS-N1 sequence."

The term "oligonucleotide" refers to a short polymer of nucleotides and/or nucleotide analogs. An "oligonucleotide reagent" of the invention includes any agent, compound or composition that contains one or more oligonucleotides, and includes, e.g., reagents comprising both single stranded and/or double stranded (ds) oligonucleotide compositions, including, e.g., single stranded RNA, single stranded DNA, DNA/DNA and RNA/DNA hybrid compositions, as well as derivatized/modified compositions thereof. Such "oligonucleotide reagents" may also include amplified oligonucleotide products, e.g., polymerase chain reaction (PCR) products. An "oligonucleotide reagent" of the invention may also include art-recognized compositions designed to mimic the activity of oligonucleotides, such as peptide nucleic acid (PNA) molecules.

The term "oligoribonucleotide" refers to a short polymer of ribonucleotides and/or ribonucleotide analogs.

An "oligoribonucleotide" of the invention can include one or a few deoxyribonucleotides or deoxyribonucleotide analogs in order to enhance the stability and/or bioaccessibility of the molecule, however, the chemical nature of the entire molecule must be primarily of a ribonucleotide nature in order that ISS-N1 blocking activity occurs absent degradation of the target RNA (i.e., absent the RNase H degradation triggered by oligodeoxyribonucleotides or DNA:RNA hybridization).

Preferably, the oligonucleotide reagent molecules/agents of the invention act (or are effective) at a concentration (e.g., have an IC50) in the nanomolar range, for example, less than 500 nM, preferably less than 400 nM, more preferably less than 300, 250, 200, 150, 100, 75, 50, 25, 10, 5, 2 or 1 nM.

Preferred oligonucleotide reagent molecules/agents are modified oligonucleotides having a length of about 5 to 50 nucleotides (or nucleotide analogs), e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides (or nucleotide analogs). In preferred embodiments, oligonucleotide reagent molecules/agents are modified oligonucleotides having a length of about 15 to 40 nucleotides (or nucleotide analogs). In other embodiments, oligonucleotide reagent molecules/agents are modified oligonucleotides having a length of about 3 to 80 nucleotides (or nucleotide analogs), or for example, about 3-10, 10-15, 15-20, 20-25, 25-30, 30-35, 35-40, 40-45, 45-50, 50-55, 55-60, 60-65, 65-70, 70-75, 75-80 or 80 or more nucleotides (or nucleotide analogs).

The term "agent" and "compound" are used interchangeably herein.

As used herein, the term "nuclease-resistant oligonucleotide" refers to any oligonucleotide that has been modified to inhibit degradation by enzymes such as, for example, the exonucleases known to be present in the cytoplasm of a eukaryotic cell. RNA molecules (e.g., RNA oligonucleotides) are particularly at risk of degradation when combined with a composition comprising a cell extract or when introduced to a cell or organism, and a "ribonuclease-resistant" oligonucleotide is thus defined as an oligonucleotide reagent molecule/agent that is relatively resistant to ribonuclease enzymes (e.g., exonucleases), as compared to an unmodified form of the same oligonucleotide. Preferred oligonucleotide reagent molecules/agents of the invention include those that have been modified to render the oligonucleotide relatively nuclease-resistant or ribonuclease-resistant. In a preferred embodiment, the oligonucleotide reagents of the invention have been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

The terms "2'-O-methyl modification", "phosphorothioate modification" and "locked nucleic acid" (LNA; oligonucleotides comprising at least one 2'-C,4'-C-oxy-methylene-linked bicyclic ribonucleotide monomer), as used herein, possess their art-recognized meanings.

The term "antisense" refers generally to any approach reliant upon agents, e.g., single-stranded oligonucleotides, that are sufficiently complementary to a target sequence to associate with the target sequence in a sequence-specific manner (e.g., hybridize to the target sequence). Exemplary uses of antisense in the instant application involve use of an oligoribonucleotide agent that hybridizes to a target pre-mRNA molecule and blocks an activity/effect (e.g., splicing pattern) of the targeted pre-mRNA sequence, but antisense approaches commonly are used to target DNA or RNA for transcriptional inhibition, translational inhibition, degradation, etc. Antisense is a technology that can be initiated by the hand of man, for example, to modulate splicing and/or silence the expression of target genes.

As used herein, the term "antisense oligonucleotide" refers to a nucleic acid (in preferred embodiments, an RNA) (or analog thereof), having sufficient sequence complementarity to a target RNA (i.e., the RNA for which splice site selection is modulated) to block a region of a target RNA (e.g., pre-mRNA) in an effective manner. In exemplary embodiments of the instant invention, such blocking of the ISS-N1 domain in SMN2 pre-mRNA serves to modulate splicing, either by masking a binding site for a native protein that would otherwise modulate splicing and/or by altering the structure of the targeted RNA. In preferred embodiments of the instant invention, the target RNA is a target pre-mRNA (e.g., SMN2 pre-mRNA). An antisense oligonucleotide having a "sequence sufficiently complementary to a target RNA sequence to modulate splicing of the target RNA" means that the antisense agent has a sequence sufficient to trigger the masking of a binding site for a native protein that would otherwise modulate splicing and/or alters the three-dimensional structure of the targeted RNA Likewise, an oligonucleotide reagent having a "sequence sufficiently complementary to a target RNA sequence to modulate splicing of the target RNA" means that the oligonucleotide reagent has a sequence sufficient to trigger the masking of a binding site for a native protein that would otherwise modulate splicing and/or alters the three-dimensional structure of the targeted RNA As used herein, the terms "ISS-N1 blocking agent," "ISS-N1 blocker," and "ISS-N1 blocking compound" refer to any agent (e.g., oligonucleotide, oligoribonucleotide, small molecule, etc.) that is capable of inhibiting the effect of the SMN2 ISS-N1 site (e.g., lessen the inhibition of SMN2 exon 7 inclusion during splicing that is caused by the ISS-N1 site).

As used herein, the term "antisense strand" as it pertains to an oligonucleotide reagent refers to a strand that is substantially complementary to a section of about 10-50 nucleotides, e.g., about 15-30, 16-25, 18-23 or 19-22 nucleotides of the pre-mRNA targeted for modulation of splicing. The antisense strand has sequence sufficiently complementary to the desired target pre-mRNA sequence to direct target-specific modulation of RNA splicing (e.g., complementarity sufficient to trigger the formation of a desired target mRNA through modulation of splicing via, e.g., altered recruitment of the splicing machinery or process).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

An oligonucleotide reagent "that directs altered RNA splicing of a gene" is an oligonucleotide that has a sequence sufficiently complementary to the target mRNA encoded by a gene to trigger altered splicing of the target mRNA by the splicing machinery or process, or, alternatively, is an oligonucleotide reagent that displaces and/or disrupts the sequence of ISS-N1.

As used herein, the term "isolated sequence" (e.g., "isolated oligonucleotide" or "isolated oligoribonucleotide") refers to sequences which are substantially free of other cellular material, or culture medium when produced by recombinant techniques, or substantially free of chemical precursors or other chemicals when chemically synthesized.

A "target gene" is a gene whose splicing is to be selectively modulated. This modulation is achieved by altering the splicing pattern of the pre-mRNA of the target gene (also referred to herein as the "target pre-mRNA") with an oligonucleotide reagent, resulting in an altered processed mRNA (the "target mRNA"). In certain embodiments, the oligonucleotide reagent is complementary, e.g., sufficiently complementary to, e.g., a section of about 18 to about 40 or more nucleotides of the pre-mRNA of the target gene to trigger the altered splicing of the pre-mRNA of the target gene. Alternatively, the oligonucleotide reagent is sufficiently homologous to the ISS-N1 sequence and/or sequences surrounding the ISS-N1 sequence to cause disruption and/or displacement of the ISS-N1 sequence from the 5' ss of a targeted exon (in preferred embodiments, SMN2 exon 7) upon sequence-specific integration (e.g., homologous recombination) at such sequences.

As used herein, the term "SMA" refers to spinal muscular atrophy, a human autosomal recessive disease that is often characterized by underexpression of SMN protein in affected individuals.

As used herein the term "compound" includes any reagent which is tested using the assays of the invention to determine whether it modulates splice site modulation, e.g., oligonucleotide reagent-mediated splicing modulation. More than one compound, e.g., a plurality of compounds, can be tested at the same time for their ability to modulate splicing in a screening assay.

In one embodiment, test compounds comprise any selection of the group consisting of a small molecule (e.g., an organic molecule having a molecular weight of about 1000 Da or less), a peptide, a polynucleotide, an antibody or biologically active portion thereof, a peptidomimetic, and a non-pepdide oligomer.

A gene "involved" in a disorder includes a gene, the normal or aberrant expression or function of which effects or causes a disease or disorder or at least one symptom of said disease or disorder.

As used herein, the term "ribozyme" refers to a nucleic acid molecule which is capable of cleaving a specific nucleic acid sequence. Ribozymes may be composed of RNA, DNA, nucleic acid analogues (e.g., phosphorothioates), or any combination of these (e.g., DNA/RNA chimerics). Within certain embodiments, a ribozyme should be understood to refer to RNA molecules that contain antisense sequences for specific recognition, and an RNA-cleaving enzymatic activity.

Various methodologies of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an oligonucleotide reagent methodology, as described herein. For example, a transcription rate, mRNA level and/or splicing pattern, translation rate, protein level, biological activity, cellular characteristic or property, genotype, phenotype, etc. can be determined prior to introducing an oligonucleotide reagent (e.g., an oligonucleotide, compound, etc., that alters splicing of target pre-mRNA in a sequence-specific manner) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. Oligonucleotide Reagents and Splice Site Alteration

The present invention is directed to oligonucleotide reagents, e.g., antisense oligonucleotides, suitable for use in blocking a domain of a target RNA (in exemplary embodiments, a pre-mRNA is blocked, thereby modulating splice site selection of the mRNA splicing machinery) both in vitro and in vivo. In vivo methodologies are useful for both general splice site modulatory purposes as well as in therapeutic applications in which blocking of a target mRNA domain (e.g., enhancement of splice site selection via oligonucleotide reagent-mediated inhibition of a splice site inhibitor domain)

is desirable. Oligonucleotide reagents of the invention are of any size and/or chemical composition sufficient to block a target RNA (e.g., pre-mRNA), in particular exemplary embodiments, the reagent is of any size and/or chemical composition sufficient to inhibit the ISS-N1 intronic splice silencing domain of SMN2. In exemplary embodiments, the oligonucleotide reagents of the invention are oligonucleotides of between about 5-300 nucleotides (or modified nucleotides), preferably between about 10-100 nucleotides (or modified nucleotides; e.g., ribonucleotides or modified ribonucleotides), for example, between about 15-35, e.g., about 15-20, 20-25, 25-30, 30-35 (31, 32, 33, 34, 35), or 35-40 nucleotides (or modified nucleotides; e.g., ribonucleotides or modified ribonucleotides). Oligonucleotide reagents are preferably sufficiently-complementary to target RNA sequences, in particular embodiments, the intronic ISS-N1 domain sequence of the SMN2 pre-mRNA. In exemplary embodiments of the invention, oligonucleotide reagents comprise oligonucleotides that contain phosphorothioate and 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) modifications. Many other forms of oligonucleotide modification may be used to generate oligonucleotide reagents of the instant invention, including, for example, locked nucleic acids (oligonucleotides comprising at least one 2'-C,4'-C-oxy-methylene-linked bicyclic ribonucleotide monomer), with one of skill in the art recognizing other modifications capable of rendering an oligonucleotide reagent effective for inducing inclusion of a target exon during RNA splicing (especially as relates to in vivo stability of the oligonucleotide reagents—refer to "Modifications" section below).

An oligonucleotide reagent can be, for example, about 5, 10, 15, 20, 25, 30, 35, 40, 45, or 50 or more nucleotides in length. An oligonucleotide reagent of the invention can be constructed using chemical synthesis and enzymatic ligation reactions using procedures known in the art. For example, an oligonucleotide reagent (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the oligonucleotide reagent can be produced biologically using an expression vector into which a nucleic acid has been sub-cloned, e.g., in an antisense orientation (i.e., RNA transcribed from the inserted nucleic acid will be of an antisense orientation to a target nucleic acid of interest, described further in the following subsection).

The oligonucleotide reagents of the invention are typically administered to a subject or generated in situ such that they hybridize with or bind to cellular pre-mRNA and/or genomic DNA comprising an ISS-N1 sequence to thereby inhibit inclusion of an exon during splicing. The hybridization can be by conventional nucleotide complementarity to form a stable duplex, or, for example, in the case of an oligonucleotide reagent which binds to DNA duplexes, through specific interactions in the major groove of the double helix. Examples of a route of administration of oligonucleotide reagents of the invention include direct injection at a tissue site or infusion of the antisense nucleic acid into an appropriately-associated body fluid, e.g., cerebrospinal fluid. Alternatively, oligonucleotide reagents can be modified to target selected cells and then administered systemically. For example, for systemic administration, oligonucleotide reagents can be modified such that they specifically bind to receptors or antigens expressed on a selected cell surface, e.g., by linking the oligonucleotide reagents to peptides or antibodies which bind to cell surface receptors or antigens. The oligonucleotide reagents can also be delivered to cells using the vectors described herein. To achieve sufficient intracellular concentrations of the oligonucleotide reagents, vector constructs in which the oligonucleotide reagent is placed under the control of a strong pol II or pol III promoter are preferred.

An oligonucleotide reagent of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The oligonucleotide reagent can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

In various embodiments, the oligonucleotide reagents of the invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675). In certain embodiments of the instant invention, PNAs can also be generated to target an ISS-N1 sequence.

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17): 3357-63). Alternatively, chimeric molecules can be synthesized with a 5' DNA segment and a 3' PNA segment (Peterser et al., 1975, *Bioorganic Med. Chem. Lett.* 5: 1119-11124).

In certain embodiments of the present invention, a PNA compound that binds to an ISS-N1 sequence can be generated additionally to contain one or more charged groups. Such tethering of charged groups to anti-ISS-N1 compounds can improve the delivery and/or activity of the anti-ISS-N1 compounds of the invention, or also can be used to minimize non-specific effects potentially associated with alternative other formulations of the oligonucleotide reagents of the instant invention. In one embodiment, the oligonucleotide reagents of the invention can be generated as phosphono-PNA molecules (pPNAs), wherein one or more phosphate groups are attached to and/or incorporated into the backbone of the oligonucleotide reagent (refer to Efimov, V., et al. 2003*Nucleosides, Nucleotides & Nucleic Acids* 22(5-8): 593-599, incorporated in its entirety herein by reference).

In further embodiments, the oligonucleotide reagents of the invention can be generated as gripNA™ compounds. GripNA™ molecules are a form of negatively charged PNA, which exhibit greater sequence specificity compared to conventional oligonucleotide reagents (e.g., antisense/gene silencing reagents) (refer to "Custom gripNA™ Synthesis Service" handbook (version B2, available through ActiveMotif at www.activemotif.com) and to U.S. Pat. No. 6,962,906, incorporated in its entirety herein by reference).

In additional embodiments, the oligonucleotide reagents of the invention can be generated as steroid-conjugated PNAs. For example, a steroid (e.g., glucocorticoid) dexamethasone can be linked to a PNA of the instant invention, as described in Rebuffat, A. G., et al. (*FASEB J.* 2002 16(11):1426-8, the entire contents of which are incorporated herein by reference). The oligonucleotide reagents of the invention can also be produced as tricycle-DNA molecules ((tc)-DNAs) that are ISS-N1 splice site-targeted, as described in Ittig, D., et al. (*Nucleic Acids Res.* 2004 32(1):346-53, the entire contents of which are incorporated herein by reference).

The oligonucleotide reagents of the invention can also be formulated as morpholino oligonucleotides. In such embodiments, the riboside moiety of each subunit of an oligonucleotide of the oligonucleotide reagent is converted to a morpholine moiety (morpholine=$C_4H_9NO$; refer to Heasman, J. 2002 *Developmental Biology* 243, 209-214, the entire contents of which are incorporated herein by reference).

The preceding forms of modifications can improve the delivery and/or activity of the oligonucleotide reagents of the invention, or also can be used to minimize non-specific effects potentially associated with alternative formulations of the oligonucleotide reagents of the instant invention.

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

In another embodiment, oligonucleotide reagents of the invention contain sequences which naturally flank the ISS-N1 sequence (i.e., sequences located at the 5' and 3' ends of the ISS-N1 sequence) in the genomic DNA of an organism. In various embodiments, the isolated oligonucleotide agent can contain about 100 kB, 50 kB, 25 kB, 15 kB, 10 kB, 5 kB, 4 kB, 3 kB, 2 kB, 1 kB, 0.5 kB or 0.1 kB of nucleotide sequences which naturally flank the ISS-N1 sequence in genomic DNA of the targeted cell. Moreover, an oligonucleotide reagent can be substantially free of other cellular material or culture medium when produced by recombinant techniques, or substantially free of chemical precursors or other chemicals when chemically synthesized.

The target RNA (e.g., pre-mRNA) blocking reaction guided by oligonucleotide reagents of the invention is highly sequence specific. In general, oligonucleotide reagents containing nucleotide sequences perfectly complementary to a portion of the target RNA are preferred for blocking of the target RNA. However, 100% sequence complementarity between the oligonucleotide reagent and the target RNA is not required to practice the present invention. Thus, the invention may tolerate sequence variations that might be expected due to genetic mutation, strain polymorphism, or evolutionary divergence. For example, oligonucleotide reagent sequences with insertions, deletions, and single point mutations relative to the target sequence may also be effective for inhibition. Alternatively, oligonucleotide reagent sequences with nucleotide analog substitutions or insertions can be effective for blocking.

Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide reagent and the target RNA, e.g., target pre-mRNA, is preferred.

In addition, variants of the ISS-N1 sequence which retain the function of ISS-N1 can be used in the methods of the invention. For example, a series of mutants of ISS-N1 were generated in Example 14 and tested for their ability to inhibit alternative splicing. Each of the mutant forms was found to retain ISS-N1 activity. In one embodiment, such variant sequences are at least about 95% identical in sequence to ISS-N1 over the entire length of the ISS-N1 15 nucleotide sequence. In another embodiment, such variant sequences are at least about 90% identical in sequence to ISS-N1 over the entire length of the ISS-N1 15 nucleotide sequence. In another embodiment, such variant sequences are at least about 85% identical in sequence to ISS-N1 over the entire length of the ISS-N1 15 nucleotide sequence. In another embodiment, such variant sequences are at least about 80% identical in sequence to ISS-N1 over the entire length of the ISS-N1 15 nucleotide sequence. In another embodiment, such variant sequences are at least about 75% identical in sequence to ISS-N1 over the entire length of the ISS-N1 15 nucleotide sequence. In another embodiment, such variant sequences are at least about 70% identical in sequence to ISS-N1 over the entire length of the ISS-N1 15 nucleotide sequence. In another embodiment, such variant sequences are at least about 66% identical in sequence to ISS-N1 over the entire length of the ISS-N1 15 nucleotide sequence.

Sequence identity, including determination of sequence complementarity for nucleic acid sequences, may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Alternatively, the oligonucleotide reagent may be defined functionally as a nucleotide sequence (or oligonucleotide sequence) a portion of which is capable of hybridizing with the target RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology,* 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Modifications

In a preferred aspect, the oligonucleotide reagents (e.g, oligoribonucleotides, such as anti-ISS-N1 oligoribonucleotides) of the present invention are modified to improve stability in serum or growth medium for cell cultures, or otherwise to enhance stability during delivery to SMA subjects and/or cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine can be tolerated without affecting the efficiency of oligonucleotide reagent-induced modulation of splice site selection. For example, the absence of a 2' hydroxyl may significantly enhance the nuclease resistance of the oligonucleotide reagents in tissue culture medium.

In an especially preferred embodiment of the present invention the oligonucleotide reagents, e.g., anti-ISS-N1 antisense molecules, may contain at least one modified nucleotide analogue. The nucleotide analogues may be located at positions where the target-specific activity, e.g., the splice site selection modulating activity is not substantially effected, e.g., in a region at the 5'-end and/or the 3'-end of the oligonucleotide (in preferred embodiments, oligoribonucleotide) molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined. Oligonucleotide reagents of the invention also may be modified with chemical moieties (e.g., cholesterol) that improve the in vivo pharmacological properties of the oligonucleotide reagents.

A further preferred oligonucleotide modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne ($—CH_2—$)$_n$ group bridging the 2' oxygen atom and the 4' carbon atom wherein n is 1 or 2. LNAs and preparation thereof are described in WO 98/39352 and WO 99/14226, the entire contents of which are incorporated by reference herein.

Within the oligonucleotide reagents (e.g., oligoribonucleotides) of the invention, as few as one and as many as all nucleotides of the oligonucleotide can be modified. For example, a 20-mer oligonucleotide reagent (e.g., oligoribonucleotide) of the invention may contain 1, 2, 3, 4, 5, 6, 7, 8, 9, 10, 11, 12, 13, 14, 15, 16, 17, 18, 19 or 20 modified nucleotides. In preferred embodiments, the modified oligonucleotides (e.g., oligoribonucleotides) of the invention will contain as few modified nucleotides as are necessary to achieve a desired level of in vivo stability and/or bioaccessibility while maintaining cost effectiveness.

RNA molecules and oligonucleotide reagents may be produced enzymatically or by partial/total organic synthesis, any modified ribonucleotide can be introduced by in vitro enzymatic or organic synthesis. In one embodiment, an RNA molecule, e.g., oligonucleotide reagent, is prepared chemically. Methods of synthesizing RNA and DNA molecules are known in the art, in particular, the chemical synthesis methods as described in Verma and Eckstein (1998) *Annul Rev. Biochem.* 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., oligonucleotide reagents, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

In preferred embodiments of the invention, the target RNA of an oligonucleotide reagent specifies the amino acid sequence of SMN protein. As used herein, the phrase "specifies the amino acid sequence" of a SMN means that the mRNA sequence is translated into a SMN amino acid sequence according to the rules of the genetic code.

By blocking domains within RNAs (e.g., pre-mRNAs) capable of being translated into such proteins, valuable information regarding the function of said oligonucleotide reagent and/or proteins and therapeutic benefits of said blocking may be obtained.

Splice forms and expression levels of surveyed RNAs and proteins may be assessed by any of a wide variety of well known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

In one embodiment, oligonucleotide reagents are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the oligonucleotide reagent. Production of oligonucleotide reagents may be targeted by specific transcription in an organ, tissue, or cell type; stimulation of an environmental condition (e.g., infection, stress, temperature, chemical inducers); and/or engineering transcription at a developmental stage or age. A transgenic organism that expresses an oligonucleotide reagent from a recombinant construct may be produced by introducing the construct into a zygote, an embryonic stem cell, or another multipotent cell derived from the appropriate organism.

II. DNA Cassettes

In certain aspects of the invention, DNA cassettes can be generated to displace and/or disrupt the ISS-N1 region via homologous recombination. Displacement and/or disruption of the ISS-N1 region in a cell can be performed by art-recognized techniques, such as chemical delivery, electroporation and/or retroviral delivery of DNA cassettes. Such DNA cassettes may be delivered to a cell in vivo or ex vivo, e.g., to neuronal and/or embryonic stem cells, which may then be reintroduced into a subject for therapeutic purpose.

III. Methods of Introducing RNAs, Vectors, and Host Cells

An oligonucleotide reagent construct of the present invention can be delivered to cells ex vivo or in vivo, for example, as an expression plasmid which, when transcribed in the cell, produces RNA, which is complementary to at least a unique portion of the cellular pre-mRNA which encodes an SMN protein.

Alternatively, the oligonucleotide reagent can be an oligonucleotide which is generated ex vivo and which, when introduced into the cell, causes inhibition of expression by hybridizing with the pre-mRNA, mRNA and/or genomic sequences of the SMN2 gene. Such oligonucleotides are preferably modified oligonucleotides, which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of oligonucleotide (see also U.S. Pat. Nos. 5,176,996, 5,294,564 and 5,256,775, which are herein incorporated by reference).

Oligonucleotide sequences can be introduced into cells as is known in the art. Transfection, electroporation, fusion, liposomes, colloidal polymeric particles and viral and non-viral vectors as well as other means known in the art may be used to deliver the oligonucleotide sequences to the cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

In certain embodiments, ribozymes can be used to deliver oligonucleotide reagents of the invention directed against ISS-N1 sequences (including functional variants of ISS-N1 sequence) to a necessary site within a given intron. Ribozyme design is an art-recognized process, described, e.g., in U.S. Pat. No. 6,770,633, the entire contents of which are incorporated by reference herein.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

As described supra and in the art, oligonucleotide reagents may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference).

Oligonucleotide reagents may be directly introduced into the cell (i.e., intracellularly); or introduced extracellularly into a cavity, interstitial space, into the circulation of an organism, introduced orally, or may be introduced by bathing a cell or organism in a solution containing the RNA using methods known in the art for introducing nucleic acid (e.g., DNA) into cells in vivo. Vascular or extravascular circulation, the blood or lymph system, and the cerebrospinal fluid are sites where the RNA may be introduced.

The present invention also provides vectors comprising an expression control sequence operatively linked to the oligonucleotide sequences of the invention. The present invention further provides host cells, selected from suitable eucaryotic and procaryotic cells, which are transformed with these vectors as necessary. Such transformed cells allow the study of the function and the regulation of malignancy and the treatment therapy of the present invention.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector. The vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al., BioTechniques 4:504-512 (1986) and include, for example, stable or transient transfection, lipofection, electroporation and infection with recombinant viral vectors. Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA completed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells providing that the viral structural proteins are supplied in trans in the packaging cell line.

Recombinant methods known in the art can also be used to achieve oligonucleotide reagent-induced inhibition of splicing in a target nucleic acid. For example, vectors containing oligonucleotide reagents can be employed to express, e.g., an antisense oligonucleotide to inhibit splicing of an exon of a targeted pre-mRNA.

Examples of methods to introduced oligonucleotide sequences into cells encompass both non-viral and viral methods, as well as in vivo and ex vivo methods and include, for example:

Direct Injection: Naked DNA can be introduced into cells in vivo by directly injecting the DNA into the cells (see e.g., Acsadi et al. (1991) *Nature* 332:815-818; Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Cationic Lipids Naked DNA can be introduced into cells in vivo by complexing the DNA with cationic lipids or encapsulating the DNA in cationic liposomes. Examples of suitable cationic lipid formulations include N-[-1-(2,3-dioleoyloxy) propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy* 2:38-49; San, H. et al. (1993) *Human Gene Therapy* 4:781-788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126). Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol.*

Cell. Biol. 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

In a preferred embodiment, a retroviral expression vector encoding an oligonucleotide of the invention is used in vivo, to thereby inhibit the activity of the ISS-N1 domain of SMN2, and thus promote SMN2 exon 7 inclusion in vivo. Such retroviral vectors can be prepared according to standard methods known in the art.

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below in subsection IV.

Cells targeted or used in the methods of the instant invention are preferably mammalian cells, in particular, human cells. Cells may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands. Neurons and muscle cells (e.g., myocytes, myoblasts, myotubes, myofibers, and the like) are preferred target cells of the invention.

Depending on the particular target gene and the dose of oligonucleotide reagent material delivered, this process may modulate function of the target gene. In exemplary embodiments of the instant invention, exon 7-containing SMN protein production is enhanced in a treated cell, cell extract, organism or patient, with an enhancement of exon 7-containing SMN protein levels of at least about 1.1-, 1.2-, 1.5-, 2-, 3-, 4-, 5-, 7-, 10-, 20-, 100-fold and higher values being exemplary. Enhancement of gene expression refers to the presence (or observable increase) in the level of protein and/or mRNA product from a target RNA. Specificity refers to the ability to act on the target RNA without manifest effects on other genes of the cell. The consequences of modulation of the target RNA can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For oligonucleotide reagent-mediated modulation of an RNA in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of modulation which is greater than 10%, 33%, 50%, 90%, 95% or 99% as compared to a cell not treated according to the present invention. Lower doses of injected material and longer times after administration of oligonucleotide reagents may result in modulation in a smaller fraction of cells (e.g., at least 10%, 20%, 50%, 75%, 90%, or 95% of targeted cells). Quantitation of gene expression in a cell may show similar amounts of modulation at the level of accumulation of target mRNA or translation of target protein. As an example, the efficiency of modulation may be determined by assessing the amount of gene product in the cell; pre-mRNA or mRNA may be detected with a hybridization probe having a nucleotide sequence outside the region used for the oligonucleotide reagent, or translated polypeptide may be detected with an antibody raised against the polypeptide sequence of that region.

The oligonucleotide reagent may be introduced in an amount which allows delivery of at least one copy per cell. Higher doses (e.g., at least 5, 10, 100, 500 or 1000 copies per cell) of material may yield more effective modulation; lower doses may also be useful for specific applications.

IV. Methods of Treatment

The present invention provides for both prophylactic and therapeutic methods of treating a subject at risk of (or susceptible to) a disorder or having a disorder associated with aberrant or unwanted target gene expression or activity (e.g., in exemplary embodiments, underexpression of SMN protein). "Treatment", or "treating" as used herein, is defined as the application or administration of a therapeutic agent (e.g., an oligonucleotide reagent (e.g., oligoribonucleotide) or vector or transgene encoding same, a small molecule ISS-N1 blocking agent, etc.) to a patient, or application or administration of a therapeutic agent to an isolated tissue or cells (including fetal cells) from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., an oligonucleotide reagent (e.g., oligoribonucleotide) or vector or transgene encoding same, a small molecule ISS-N1 blocking agent, etc.). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., an oligonucleotide reagent (e.g., oligoribonucleotide) or vector or transgene encoding same, a small molecule ISS-N1 blocking agent, etc.) that is specific for the target gene or protein (e.g., is specific for the pre-mRNA encoded by said gene and/or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Modulation of target gene activity is desirable in situations in which target gene is abnormally unregulated and/or in which altered target gene activity is likely to have a beneficial effect.

In one embodiment, cells from a subject having spinal muscular atrophy are contacted with an oligonucleotide reagent of the invention to inhibit splicing of the SMN2 exon 7. Exemplary oligonucleotide reagents include sequences complementary to the ISS-N1 sequence and variants thereof (e.g., as shown in Example 14). In another embodiment, cells from a subject having another disorder that would benefit from inhibition of alternative splicing are contacted with an oligonucleotide reagent of the invention. Target sequences related to the ISS-N1 sequence are present in human intronic sequences. For example, there is a sequence partially homologous to the ISS-N1 -sequence located in human CFTR (intron 10). Additional exemplary genes that can be targeted by oligonucleotide reagents of the invention (e.g., sequences complementary to the ISS-N1 sequence and variants thereof (e.g., as shown in Example 14) include, but are not limited to, CFTR, FAS, Caspases, Diablo, NF1, Bc12, Tau, ApoA-11, p53, Tra2, Cox-1 and Survivin.

3. Delivery of Oligonucleotide Reagents to the Nervous System

The oligonucleotide reagents of the invention can be delivered to the nervous system of a subject by any art-recognized method. For example, peripheral blood injection of the oligonucleotide reagents of the invention can be used to deliver said reagents to peripheral neurons via diffusive and/or active means. Alternatively, the oligonucleotide reagents of the invention can be modified to promote crossing of the blood-brain-barrier (BBB) to achieve delivery of said reagents to neuronal cells of the central nervous system (CNS). Specific recent advancements in oligonucleotide reagent technology and delivery strategies have broadened the scope of oligonucleotide reagent usage for neuronal disorders (Forte, A., et al. 2005. *Curr. Drug Targets* 6:21-29; Jaeger, L. B., and W. A. Banks. 2005. *Methods Mol. Med.* 106:237-251; Vinogradov, S. V., et al. 2004. *Bioconjug. Chem.* 5:50-60; the preceding are incorporated herein in their entirety by reference). For example, the oligonucleotide reagents of the invention can be synthesized to comprise phosphorothioate oligodeoxynucleotides (P-ODN) directed against ISS-N1, or may be generated as peptide nucleic acit (PNA) compounds. P-ODN and PNA reagents have each been identified to cross the BBB (Jaeger, L. B., and W. A. Banks. 2005. *Methods Mol. Med.* 106:237-251). Treatment of a subject with, e.g., a vasoactive agent, has also been described to promote transport across the BBB (ibid.). Tethering of the oligonucleotide reagents of the invention to agents that are actively transported across the BBB may also be used as a delivery mechanism (ibid.).

In certain embodiments, the oligonucleotide reagents of the invention can be delivered by transdermal methods (e.g., via incorporation of the oligonucleotide reagent(s) of the invention into, e.g., emulsions, with such oligonucleotide reagents optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The oligonucleotide reagents of the invention may also be delivered via an implantable device (e.g., pacemaker or other such implantable device). Design of such a device is an art-recognized process, with, e.g., synthetic implant design described in, e.g., U.S. Pat. No. 6,969,400, the contents of which are incorporated in their entirety by reference herein.

4. Pharmacogenomics

The therapeutic agents (e.g., an oligonucleotide reagent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an oligonucleotide reagent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

V. Pharmaceutical Compositions

The invention pertains to uses of the above-described agents for therapeutic treatments as described infra. Accordingly, the modulators of the present invention (e.g., oligonucleotides, small molecules and the like) can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

The following materials, methods, and examples are illustrative only and not intended to be limiting.

Materials and Methods

In general, the practice of the present invention employs, unless otherwise indicated, conventional techniques of chemistry, molecular biology, recombinant DNA technology, and standard techniques in electrophoresis. See, e.g., Sambrook, Fritsch and Maniatis, Molecular Cloning: Cold Spring Harbor Laboratory Press (1989) and Current Protocols in Molecular Biology, eds. Ausubel et al., John Wiley & Sons (1992).

Figures 1, 11:
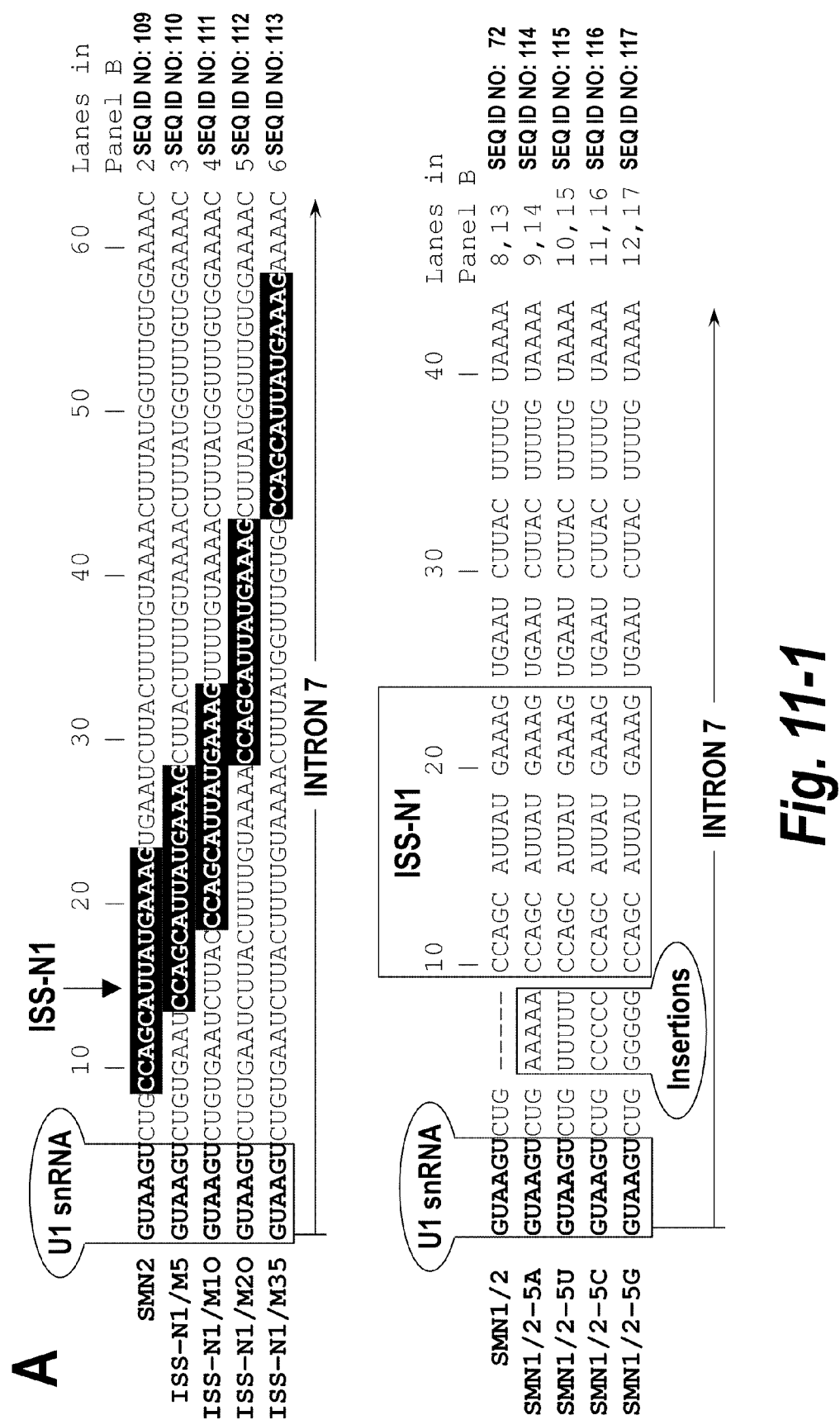
Figures 2, 11:
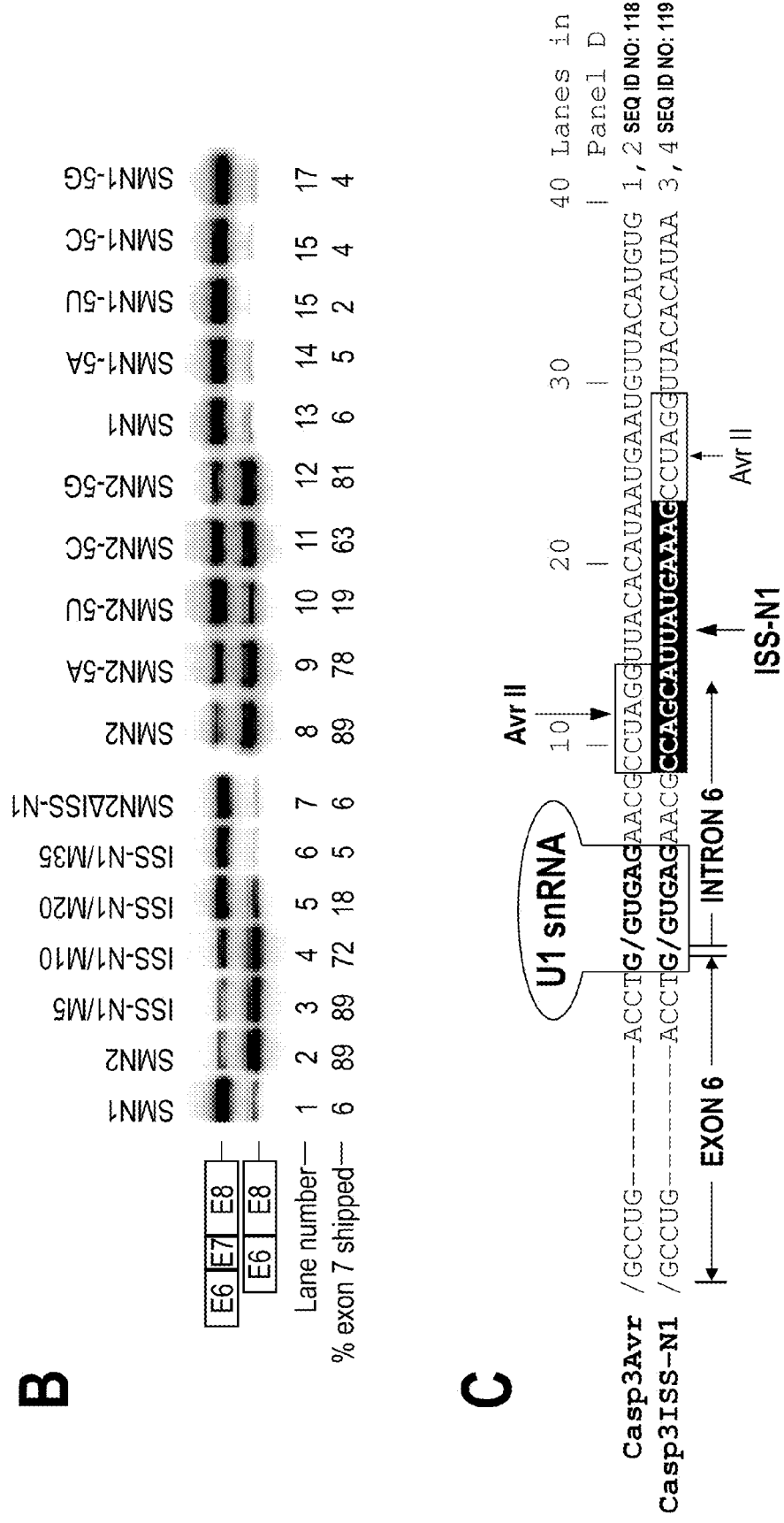
FIGS. 11A-D demonstrate the portability of the ISS-N1 element.
Figures 3, 11:
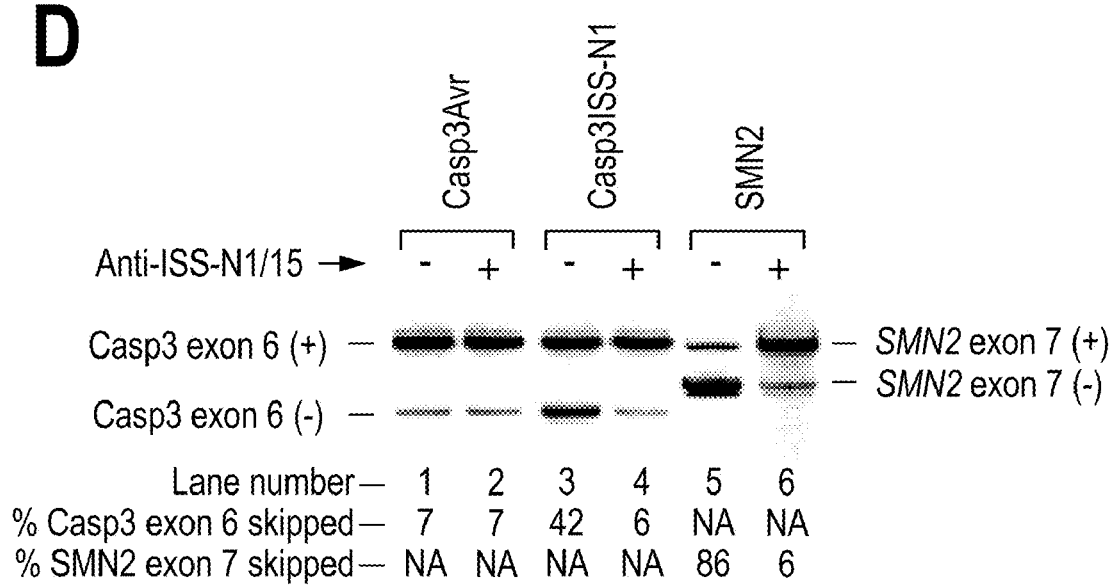

Minigenes. Minigene splicing cassettes pSMN1ΔI6 and pSMN2ΔI6 were constructed by deleting approximately 6 kb within intron 6 from pSMN1 and pSMN2, respectively (Singh, N.N., et al. 2004. *Biochem. Biophys. Res. Commun.* 315:381-388). In certain of the following Examples, SMN1 and SMN2 refer to pSMN1ΔI6 and pSMN2 ΔI6, respectively, described previously (ibid.). Mutations were generated by PCR using the strategy described in Singh, N.N., et al. 2004. *Biochem. Biophys. Res. Commun.* 315:381-388. Minigene splicing cassette Casp3 was constructed by amplifying genomic sequences spanning exon 5 to exon 7 of the Caspase 3 gene, using high fidelity Pfx polymerase (Invtrogen), genomic DNA (Clontech) and a pair of primers P53 (GTCCTCGAGTTTCTAAAGAAGATCACAGC, SEQ ID NO: 7) and P56 (GTCGCGGCCGCACCATCTTCTCACTTGGCAT, SEQ ID NO: 8). The resulting PCR fragment was subsequently digested with Xho I and Not I (NEB) and cloned into pCI vector (Promega). Minigene splicing cassette Casp3Avr was generated by inserting an Avr II restriction site (CCTAGG) in Casp3 minigene downstream of an alternatively-spliced exon 6 using high fidelity PCR. Minigene splicing cassette Casp3ISS-N1 was generated by inserting an ISS-N1 sequence (CCAGCATTATGAAAG, SEQ ID NO: 9) using Avr II restriction site in Casp3Avr. The exact locations of Avr II and/or ISS-N1 sites are shown in FIG. 11C. Splicing cassettes pTBEx9-V456F (CFTR exon 9 splicing), pTBEx12-50A (CFTR exon 12 splicing) and pTBApoISE3m (apoA-II exon 3 of splicing) were the same as in Mercado, P.A., et al. 2005. *Nude. Acids Res.* (in Press); Pagani, F., et al. 2003. *J. Biol. Chem.* 278:26580-26588; Pagani, F., et al. 2003. *Hum. Mol. Genet.* 12:1111-1120. Splicing cassettes CMV-Fas (wt) and CMV-Fas mutant (U-20C) (Fas exon 6 splicing) were the same as in Izquierdo, J.M., et al. 2005. *Mol. Cell* 19:475-484. Splicing cassette SI9/LI10 (Tau exon 10 splicing) was the same as in Yu, Q., et al. 2004. *J. Neurochem.* 90:164-72.

Cell culture. Unless otherwise stated, all tissue culture media and supplements were purchased from Invitrogen. Human cervical carcinoma (C33a) cells, human HEK-293 cells and mouse motor-neuron-like (NSC-34) cells were cultured in Dulbecco's modified Eagle's medium (DMEM) supplemented with 10% fetal bovine serum (FBS), 100 units/ml penicillin and 100 µg/ml streptomycin. Human neuroblastoma (SK-N-SH) cells were maintained in 1:1 mixture of Minimum Essential Medium (MEM) and Ham's F12 medium supplemented with 10% FBS. Mouse neuroblastoma (Neuro-2a) cells were grown in MEM supplemented with 2 mM L-glutamine, 0.1 mM non-essential amino acids, 1.0 mM sodium pyruvate and 10% FBS. Mouse teratocarcinoma (P19) cells were maintained in alpha-MEM supplemented with 10% FBS. All cells mentioned above were obtained from the American Type Culture Collection. NSC-34 cells were obtained from Dr. Neil Cashman (University of Toronto). Primary fibroblast cell line from SMA type I patient (GM03813) and a healthy control (AG06814) were obtained from Coriell Cell Repositories. These cell lines were maintained in MEM supplemented with 2 mM L-glutamine and 15% FBS.

```
Anti-N1:
                                        (SEQ ID NO: 10)
5'-mA*mU*mU*mC*mA*mC*mU*mU*mU*mC*mA*mU*mA*mA*mU*
mG*mC*mU*mG*mG3';

Anti-N1 + 10:
                                        (SEQ ID NO: 11)
5'-mC*mA*mA*mA*mA*mG*mU*mA*mA*mG*mA*mU*mU*mC*mA*
mC*mU*mU*mU*mC3';

Anti-N1 + 20:
                                        (SEQ ID NO: 12)
5'-mU*mA*mA*mA*mG*mU*mU*mU*mU*mA*mC*mA*mA*mA*mA*
mG*mU*mA*mA*mG3';

Anti-N1 + 30:
                                        (SEQ ID NO: 13)
5'-mC*mC*mA*mC*mA*mA*mA*mC*mC*mA*mU*mA*mA*mA*mG*
mU*mU*mU*mU*mA3';

Scramble20:
                                        (SEQ ID NO: 14)
5'-mU*mC*mC*mU*mU*mU*mA*mA*mA*mG*mU*mA*mU*mU*mG*
mU*mG*mA*mC*mC3';

Anti-17-25:
                                        (SEQ ID NO: 15)
5'-mA*mU*mU*mC*mA*mC*mU*mU*mU*mC*mU*mA*mA*mA*mU*
mU*mA*mA*mG*mG3';

Anti-ISS-N1/15:
                                        (SEQ ID NO: 16)
5'-mC*mU*mU*mU*mC*mA*mU*mA*mA*mU*mG*mC*mU*mG*mG-3'
```

The abbreviation "m" represents O-methyl modification at the 2nd position of sugar residue, whereas "*" represents a phosphorothioate modification of the backbone. Scramble20 and Anti-N1 had the same sequence composition: three guanosines, four cytosines, five adenosines and eight uridines.

Transfections and in vivo splicing assays. All reagents were used according to manufacturer's recommendations. Transient transfections of cells with plasmid DNA or antisense oligonucleotides were performed using Lipofectamine™ 2000 (Invitrogen). Cells were plated 24 hours prior to transfection so that their density on the day of transfection was approximately 90%. For co-transfection experiments, cells were transfected with the indicated amounts of plasmid DNA and an oligonucleotide of interest. Oligonucleotide concentration ranged from 25 to 500 nM. In a given experiment, the total amount of oligonucleotide was maintained constant by adding control oligonucleotide (Scramble20). Unless indicated otherwise, total RNA was isolated 24 hours after transfection using Trizol™ reagent (Invitrogen). To generate cDNA, reverse-transcription was carried out using the SuperScript™ II reaction kit (Invitrogen). Oligo (dT) primer was used in case of pCI-based minigenes, while random hexamers and vector-specific 3' primer PT2 (5'AAGCTTGCATCGAATCAGTAG3', SEQ ID NO: 17) were used in the case of pTB-vector-based minigenes and Fas minigenes, respectively. Generally, 1.0 µg of total RNA was used per 20 µl of reaction. Minigene-specific spliced products were subsequently identified using Taq polymerase (Invitrogen) and the following primer combinations: P1 (5'CGACTCACTATAGGCTAGCC3', SEQ ID NO: 18) and P2 5'GCATGCAAGCTTCCTTTTTTCTTTCCCAACAC3', SEQ ID NO: 19) for SMN minigenes (Singh, N.N., et al. 2004. *Biochem. Biophys. Res. Commun.* 315:381-388); alfa-23 (5'CAACTTCAAGCTCCTAAGCCACTGC3', SEQ ID NO: 20) and BRA2 (5'TAGGATCCGGTCACCAGGAAGT-TGGTTAAATCA3' (SEQ ID NO: 21) for CFTR and apoA-II minigenes (Mercado, P.A., et al. 2005. *Nucle. Acids Res.* (in Press); Pagani, F., et al. 2003. *J. Biol. Chem.* 278:26580-26588; Pagani, F., et al. 2003. *Hum. Mol. Genet.* 12:1111-1120); FP (5'GGTGTCCACTCCCAGTTCAA3', SEQ ID NO: 22) and RP (5'CCCTGGTTTATGATGGATGTTGC-CTAATGAG3', SEQ ID NO: 23) for Tau minigene (Yu, Q., et al. 2004. *J. Neurochem.* 90:164-72); P1 and P56 for Casp3 minigenes; PT1 (5'GTCGACGACACTTGCTCAAC3', SEQ ID NO: 24) and PT2 for Fas minigenes (Izquierdo, J.M., et al. 2005. *Mol. Cell* 19:475-484). Analysis and quantifications of spliced products were performed using a FPL-5000 Image Reader and ImageGauge software (Fuji Photo Film Inc.; Singh, N.N., et al. 2004. *Biochem. Biophys. Res. Commun.* 315:381-388). Results were confirmed by three independent experiments.

Expression of endogenous genes. For GM03813 and AG06814 fibroblast transfection, cells were plated at a density of ~0.3×10⁵ per one well of a 24-well plate one day before transfection. Cells were then transfected with an indicated oligonucleotide (from 5 to 200 nM). Total oligonucleotide amount was held constant by adding scrambled oligonucleotide (Scramble20). Unless indicated otherwise, total RNA was isolated 24 hours after transfection using Trizol reagent (Invitrogen). Reverse-transcription was carried out using oligo (dT) primer and SuperScript™ II (Invitrogen) as described above. For PCR amplification of endogenous exons, the following primer combinations were used: N-24 (5'CCAGATTCTCTTGATGATGCTGATGCTTTGGG3', SEQ ID NO: 25) and P2 (5'GCATGCAAGCTTC-CTTTTTTCTTTCCCAACAC3', SEQ ID NO: 26) for SMN exon 7; Ex4Sense (5'CGGAATTCCAATGAAAAT-GAAAGCCAAGTTTCAAC3', SEQ ID NO: 27) and Ex6Anti (5'ATAGTTTAGCGGCCGCCATATAATAGC-CAGTATGATAG3', SEQ ID NO: 28) for SMN exon 5; Ex1Sense (5'CGGAATTCCATGGCGATGAGCAGCG-GCGGCAG3', SEQ ID NO: 29) and Ex4Anti (5'ATAGTT-TAGCGGCCGCCTTTCCTGGTCCCAGTCTTGG3', SEQ ID NO: 30) for SMN exon 3; P53 and P56 for Caspase 3 exon 6; 5'-Sur (GCATGGGTGCCCCGACGTTG, SEQ ID NO: 31) and 3'-Sur (GCTCCGGCCAGAGGCCTCAA, SEQ ID NO: 32) for Survivin exons 2B/3 (Mahotka, C., et al. 1999. *Cancer Res.* 59:6097-6102); A1 (CATGAGCGACAGCG-GCGAGCAGAA, SEQ ID NO: 33) and A3 (TTAATAGC-GACGAGGTGAGTA, SEQ ID NO: 34) for Tra2 exons 2a/2b (Chen, X., et al. 2003. *Cell Biol. Int.* 27:491-496); 5'Bcl-X (CATGGCAGCAGTAAAGCAAG, SEQ ID NO: 35) and 3'Bcl-X (GCATTGTTCCCATAGAGTTCC, SEQ ID NO: 36) for Bcl-x exon 2 (Mercatante, D.R., et al. 2002. *J. Biol Chem.* 277:49374-49382); ex28F (GGAGTACACCAAG-TATCATGAG, SEQ ID NO: 37) and ex31R (CATTATGCT-TGCAAAAACGAAC, SEQ ID NO: 38) for NF1 exons 29/30 (Park, V.M., et al. 1998. *Hum. Genet.* 103:382-385). Results were confirmed by three independent experiments.

Antibodies and western blot analysis. Transfections with antisense oligonucleotides were done as described above. For each sample, the same number of cells (~9×10⁵) was harvested 72 hours after transfection and lysates were prepared as in Elbashir, S. M., et al. 2002. *Methods* 26:199-213. One third of each lysate was used for one blot. Lysates were electrophoresed on a 10% (w/v) SDS-PAGE gel and the proteins were transferred onto polyvinylidene fluoride (PVDF) membrane (Pall Life Sciences). The protein transfer and equal loading were verified by SYPRO Ruby protein blot staining (Bio-Rad Laboratories). The membranes were blocked with 5% non-fat dried milk in TBST (20 mM Tris, 150 mM NaCl and 0.1% Tween 20) overnight at 4° C. and subsequently incubated with primary anti-SMN antibodies (BD Transduction Laboratories) followed by washing and incubation with horseradish peroxidase-conjugated goat anti-mouse IgG (Jackson Immunoresearch). For a loading control, membranes were stripped with buffer containing 10 mM Tris, 75 mM NaCl, 1% SDS and 10 mM β-mercaptoethanol (30 minutes at 60° C.) and re-probed for α-tubulin. Monoclonal antibodies against α-tubulin were from Sigma. Immunoreactive proteins were visualized using SuperSignal West Dura Extended Duration Substrate (Pierce). The membranes were scanned using a LAS-1000 Image Reader (Fuji Photo Film Inc.). Results were confirmed by three independent experiments.

Example 1

In Vivo Selection of the Entire Exon 7 Revealed Novel Cis-Elements

Understanding the mechanism of splicing of exon 7 in SMN genes is important for development of mechanism-based therapeutic strategies. Towards this goal, the entire exon 7 of SMN2 was examined using a state of the art method of in vivo selection (the selection process was performed on a pool of minigene sequences comprising partially randomized exon 7 sequences, with iterative selection across individual rounds of PCR and size separation for exon 7-containing SMN2 mutants; for further details, refer to Singh et al., RNA 10, 1291-1305). Three major cis-acting elements were identified by this selection process (termed Exinct, Conserved tract, and 3'—Cluster; refer to FIG. 1). The putative binding sites of SF2/ASF (Cartegni, L., and A. R. Krainer. 2002. *Nat. Genet.* 30:377-384) and hnRNP-A1 (Kashima, T., and J. L. Manley. 2003. *Nat. Genet.* 34:460-463) fell within the inhibitory cis-element "Exinct". Meanwhile, the binding site of Tra2-β1 (Hofmann, Y., et al. 2000. *Proc. Natl. Acad. Sci. USA* 97:9618-23) fell within the stimulatory cis-element "Conserved Tract". Consistent with a recent report that revealed the presence of an extended inhibitory context (termed 'Exinct') at the 5' end of exon 7, in vivo selection showed the longest tract of mutable residues at the 5' end of exon 7 (Singh et al., RNA 10, 1291-1305). Most importantly, in vivo selection revealed a novel 7-nucleotide-long inhibitory region towards the 3' end of exon 7, which was named "3'-Cluster" (Singh et al., RNA 10, 1291-1305). This cluster spans positions 45 through 51 and includes the translation termination codon. It also includes the last residue of a leucine codon that is not evolutionarily conserved among mammalian exon 7 (Singh et al., RNA 10, 1291-1305). Deletion of leucine codon promoted exon 7 inclusion in SMN2, whereas deletion of the preceding codon had no effect, suggesting a specific role of nucleotides that were gained (or retained) during evolution. Another interesting feature of in vivo selection was the identification of a long-conserved tract in the middle of exon 7. Supporting the stimulatory role of the long conserved tract, many mutations within this tract led to exon 7 exclusion in SMN1 (Singh et al., RNA 10, 1291-1305). These results suggested that the long conserved tract contains many overlapping stimulatory cis-elements, some of which could be tissue-specific.

Example 2

Exon 7 has a Weak 5' Splice Site (ss)

The 5' splice site (ss) of exon 7 is defined by sequences that are located at the junction of exon 7 and intron 7. One of the noteworthy outcomes of in vivo selection of the entire exon 7 was the discovery of the extremely weak nature of the 5' ss (Singh et al., RNA 10, 1291-1305). It was surprising to observe the strong impact of a single nucleotide substitution (A54G at the last position of exon 7) that not only restored exon 7 inclusion in SMN2, but also obviated the requirement of other regulatory elements. These results showed that a weak 5' ss of exon 7 served as the limiting factor for exon 7 inclusion in SMN2, and this weak 5' ss thereby facilitated exon 7 exclusion in SMN2.

Example 3

Sub-Optimal U1 snRNA Base Pairing Contributes to the Weak 5' ss of Exon 7

U1 snRNA is the RNA component of the U1 snRNP, which is abundantly present in all cell types and plays a critical role in pre-mRNA splicing. Loss or gain of U1 snRNA base pairing has been directly linked to genetic disorders (Grover et al., J. Biol. Chem. 274, 15134-15143; Pagani et al., Nat. Genet. 30, 426-429; Manabe et al., Cell Death Differ. 10, 698-708). Having demonstrated the weak 5' ss of exon 7 in SMN genes (Singh et al., RNA 10, 1291-1305), the potential role of poor U1 snRNA base-pairing was examined as one of the possible causes of exon 7 exclusion in SMN2. To test this hypothesis, a mutant U1 snRNA was constructed that increased the length of the complementary region from 6 to 11 nucleotides. Upon co-transfection with SMN2, this mutant U1 snRNA promoted exon 7 inclusion to the level of SMN1. The sequence-specific effect was confirmed by co-transfection with the wild-type U1 snRNA or an empty vector, which did not promote exon 7 inclusion. Interestingly, the mutant U1 snRNA was also able to compensate for the loss of ESE associated with Tra2. The mutant U1 snRNA also overcame the inhibitory effects of G1H mutations, which have been recently shown to be inhibitory (Singh et al., RNA 10, 1291-1305). Additionally, intronic mutations that extended U1 snRNA base-pairing promoted exon 7 inclusion in SMN2, further supporting the critical role of U1 snRNA base-pairing. These results confirmed the poor recruitment of U1 snRNP at the 5' ss of exon 7 as the major cause of exon 7 exclusion in SMN2. Multiple factors likely contribute to poor recruitment of the U1 snRNP. Such factors include the role of RNA structure, which also defines the accessibility of the 5' ss of the alternatively spliced exon. Role of RNA structure is well documented in alternative splicing of exon 10 of tau, which is implicated in Fronto-Temporal Dementia associated with Parkinsonism (Grover et al., J. Bio. Chem. 274, 15134-15143). Additional factors that bind to intronic sequences downstream of the U1 snRNA binding site were accordingly predicted to play a role in affecting the accessibility of U1 snRNP.

Example 4

Identification of an Intronic Splicing Silencer (ISS) within Intron 7

Figure 3:
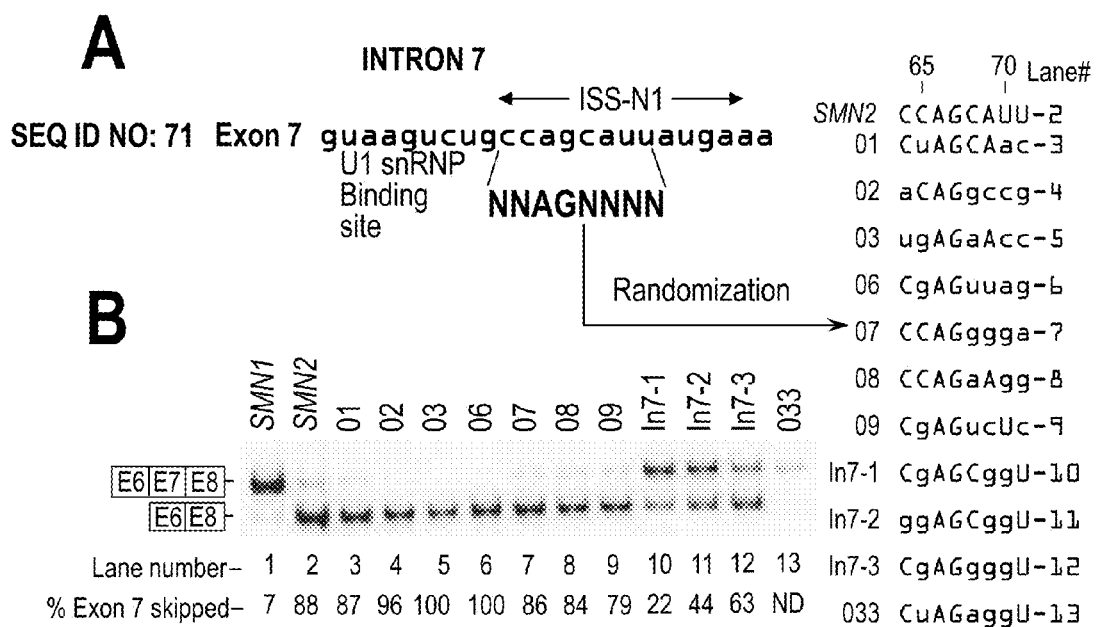
FIGS. 3A and B depict the randomization and selection approach used to analyze the eight-nucleotide-long intronic cis-element ISS-N1 (which lies just after the U1 snRNA binding site at the 5' ss of intron 7).
FIG. 3B shows the SMN2 splicing pattern of these randomly-picked eleven clones, with mutant 033 demonstrated to fully restore exon 7 inclusion in the processed SMN2 transcript.
Figures 2, 4:
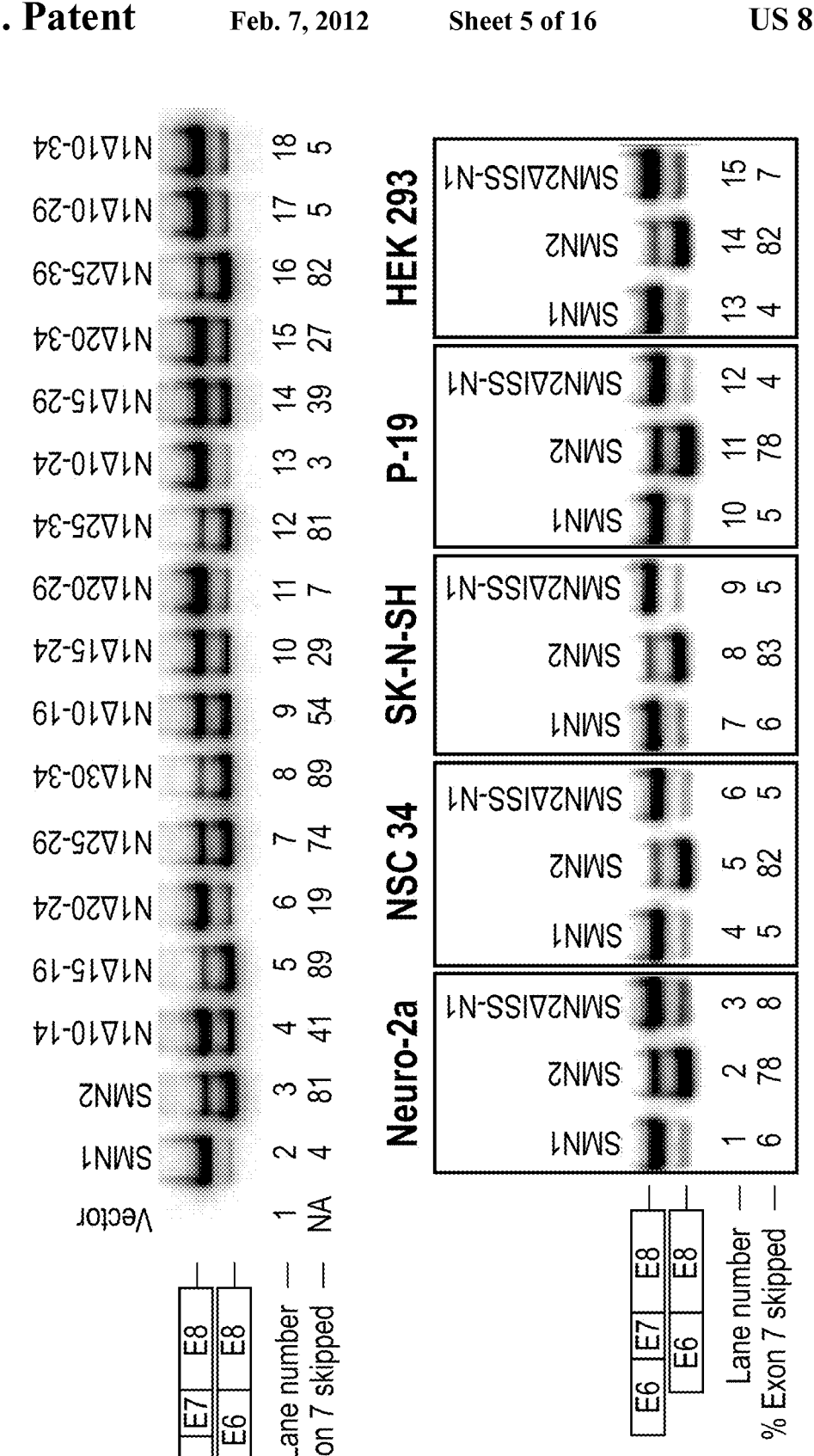
FIGS. 4A-C show the effect of intronic deletions downstream of the 5' ss of exon 7 of SMN2.
Figure 5:
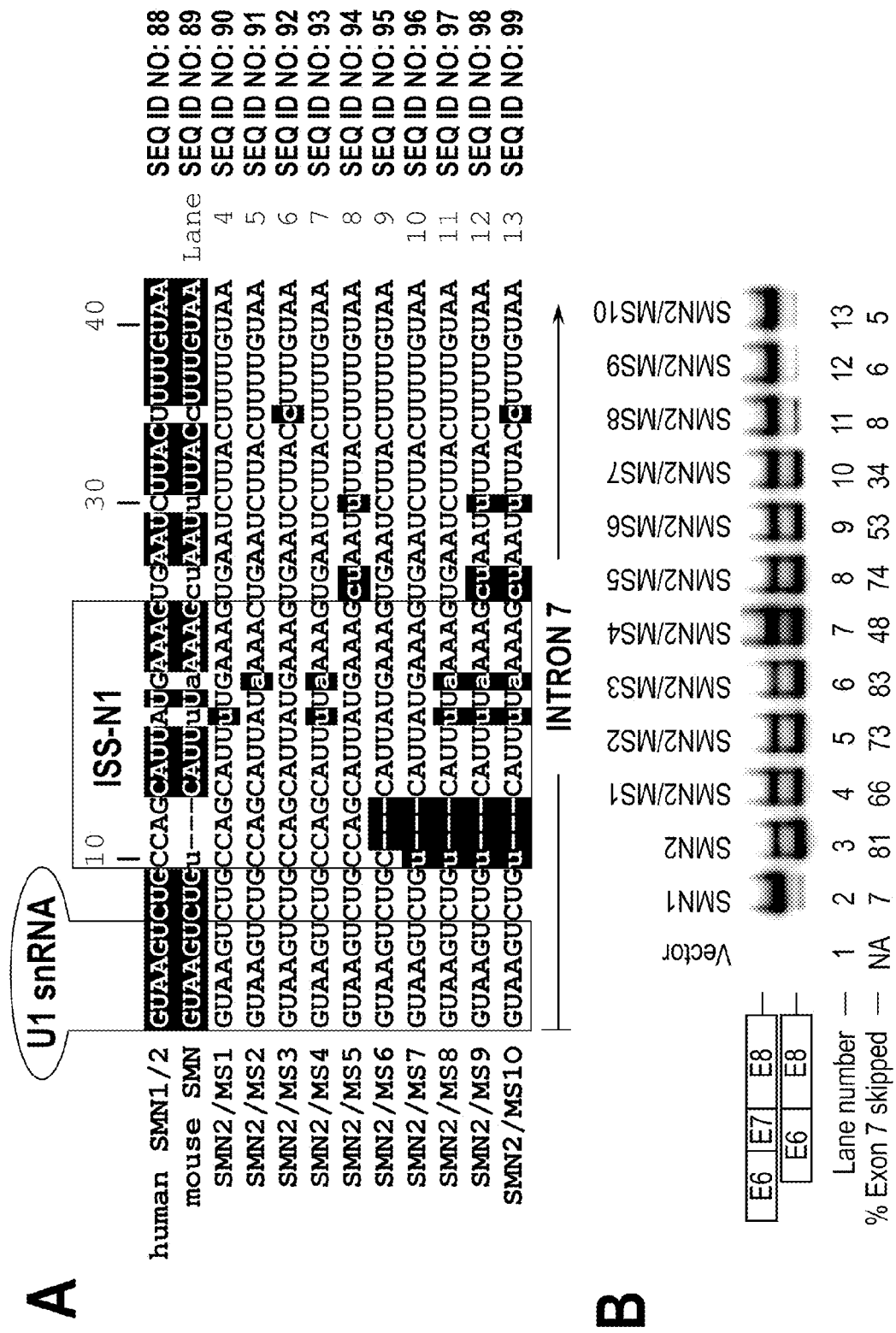
FIGS. 5A and B display the evolutionary significance of ISS-N1.
FIG. 5B shows the in vivo splicing pattern of SMN2 mutants shown in FIG. 5A, with spliced products the same as indicated in FIG. 4B.
Figure 6:
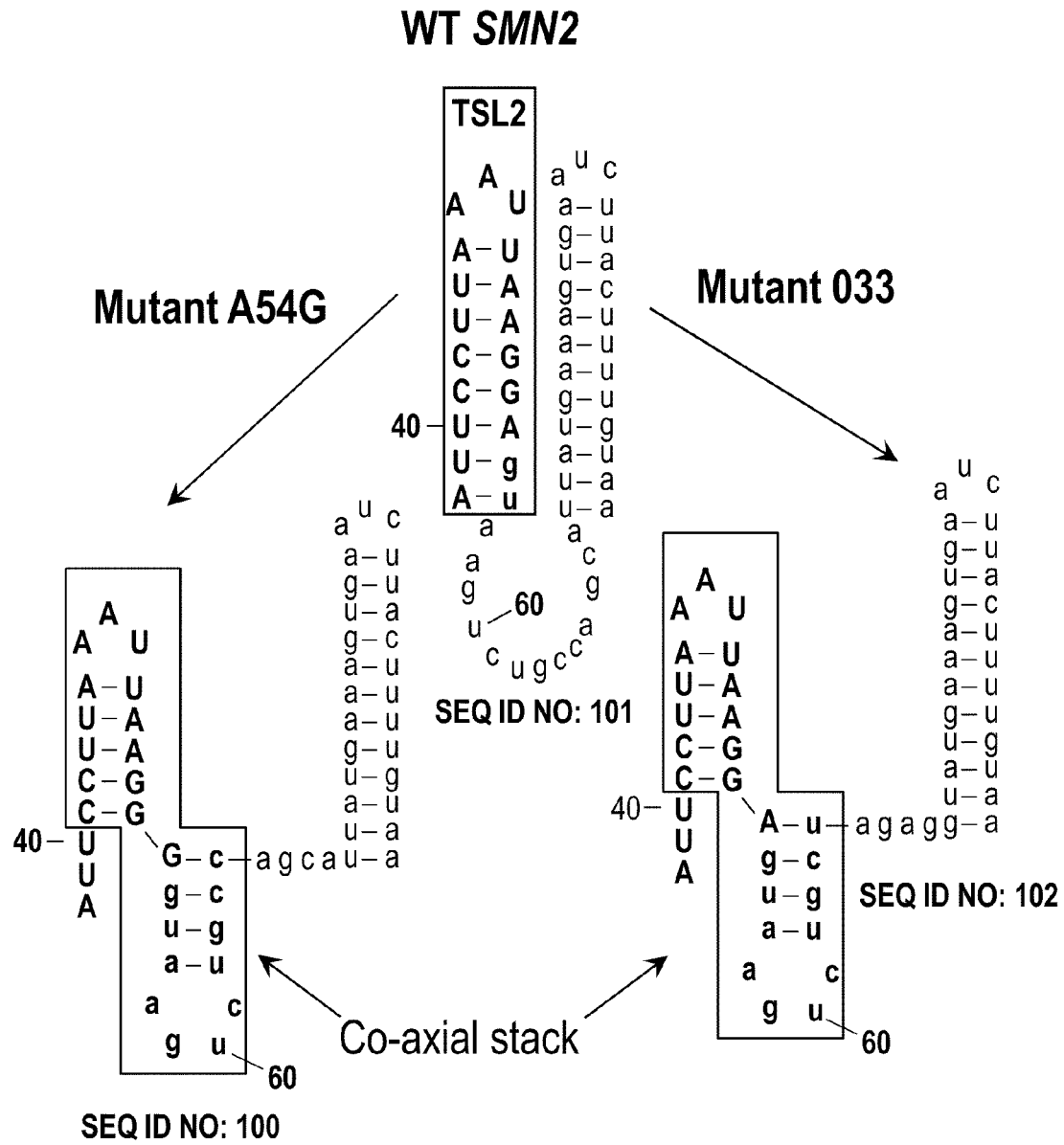
FIG. 6 schematically depicts the RNA structure of wild-type (SEQ ID NO: 101), mutant 033 (SEQ ID NO: 102) and mutant A54G (SEQ ID NO: 100) pre-mRNAs. Numbering starts from exon 7. Exon 7 sequence is shown in upper-case letters, while intron 7 sequences are shown in lower-case letters. The stem loop structure of TSL2 is shaded dark, while light-shaded regions are regions of co-axial stacking.

Intronic cis-elements as the regulators of alternative splicing have been documented in many systems (see e.g., Lou et al., Mol. Cell. Biol. 15, 7135-7142; Nishiyama et al., J. Bone Miner. Res. 18, 1716-1722). In the case of SMN genes, two intronic elements that modulate exon 7 splicing have been identified (Miyajima, H., et al. 2002. J. Biol. Chem. 277: 23271-23277; Miyaso, H., et al. 2003. J. Biol. Chem. 278: 15825-15831). However, the trans-acting factors interacting at these elements have not been characterized. Having confirmed the critical role of U1 snRNA binding at the 5' ss of exon 7, discovery of previously unidentified intronic elements that contribute to the suboptimal 5' ss of exon 7 was prioritized. In initial studies to accomplish this goal, random deletions/mutations were made at different locations within intron 7. While deletions/mutations at most locations had only marginal effect on exon 7 inclusion in SMN2, one site was identified to show improved exon 7 inclusion following deletion/mutation. This domain was termed the Intronic Splicing Silencer N1 ("ISS-N1", a sequence comprising 5'-CCAGCAUU-3' (SEQ ID NO: 1; refer to SEQ ID NO: 3, "5'-CCAGCAUUAUGAAAG-3')) and was located just after the U1 snRNA binding site at the 5' ss of intron 7 (FIG. 3A). To further characterize this silencer element, a randomization-and-selection approach was adopted in which a small sequence stretch was first randomized to create a combinatorial library of SMN2 mutants. About 50 mutants were analyzed for in vivo splicing activity. One mutant fully restored exon 7 inclusion in SMN2, supporting the inhibitory nature of ISS-N1 (FIG. 3B, mutant '033'). To explore further whether an intronic cis-element contributed towards the weak 5' ss, SMN2 minigene mutants with different deletions at the 5' end of intron 7 were generated. The in vivo splicing pattern of these mutants was then determined, using the highly transfectable cell line C33a (FIG. 4B). In all the deletions, the first nine nucleotides of intron 7 were retained. These nucleotides are conserved among mammals and harbor the canonical base-pairing region for U1 snRNA, a component of U1 snRNP. First, five-nucleotide-long deletions between positions 10 and 34 were made (mutants N1Δ10-14, N1Δ15-19, N1Δ20-24, N1Δ25-29 and N1Δ30-34, FIG. 4B, lanes 4-8). Analysis of these mutants revealed two inhibitory stretches from positions 10 to 14 (CCAGC) and from 20 to 24 (GAAAG), separated by a five-nucleotide sequence (AUUAU). Deletion of GAAAG produced the strongest stimulatory effect (mutant N1Δ20-24; FIG. 4B, lane 6), whereas deletion of CCAGC produced a moderate but noticeable stimulatory effect (mutant N1Δ10-14; FIG. 4B, lane 4). Deletion of AUUAU produced no stimulatory effect (mutant N1Δ15-19; FIG. 4B, lane 5), indicating that this deletion likely strengthened an inhibitory element by bringing the flanking sequences CCAGC and GAAAG together. Indeed, when AUUAU was deleted together with either CCAGC or GAAAG, SMN2 exon 7 inclusion increased (mutants N1Δ10-19 and N1Δ15-24; FIG. 4B, lanes 9 and 10, respectively). In general, ten or fifteen nucleotide deletions that did not include CCAGC or GAAAG produced no stimulatory effect on exon 7 inclusion (mutants N1Δ25-34 and N1Δ25-39; FIG. 4B, lanes 12 and 16, respectively).

Figure 7:
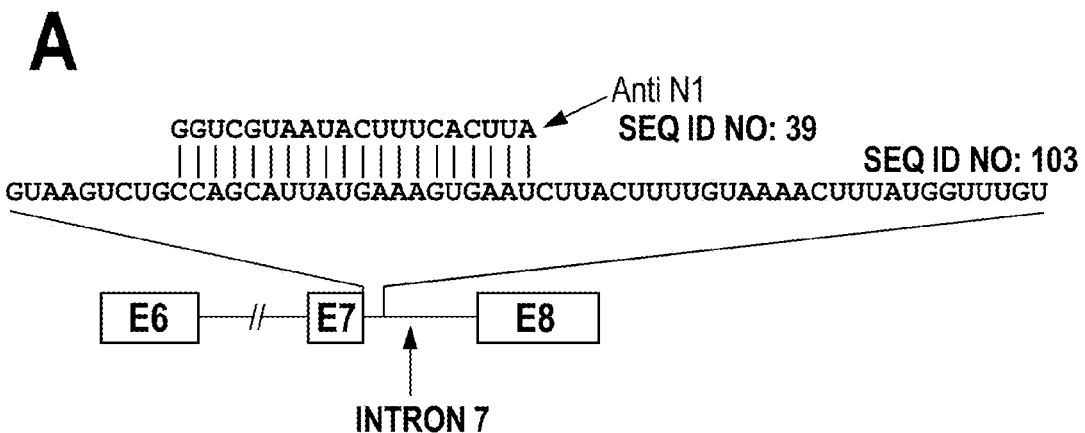
FIGS. 7A-C depict the effect of treatment with an antisense oligonucleotide (anti-N1) on splicing of exon 7 in SMN2.
Figure 7:
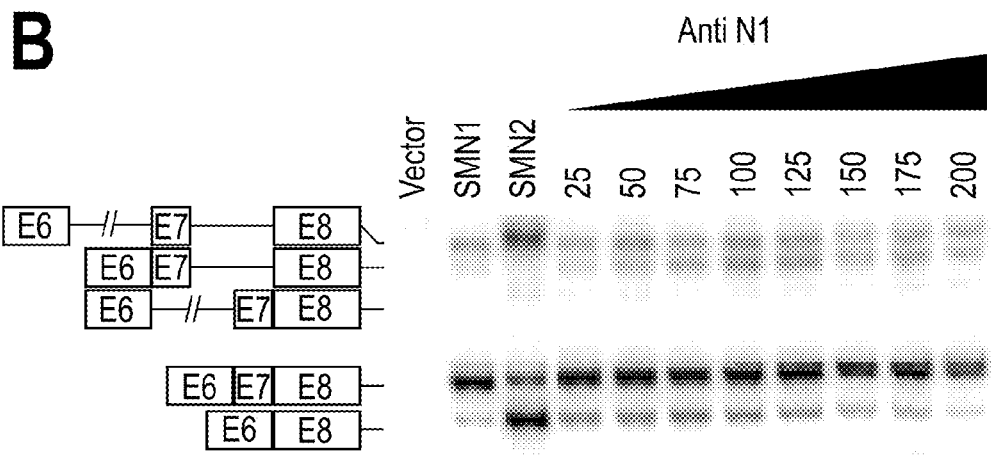
Figure 7:
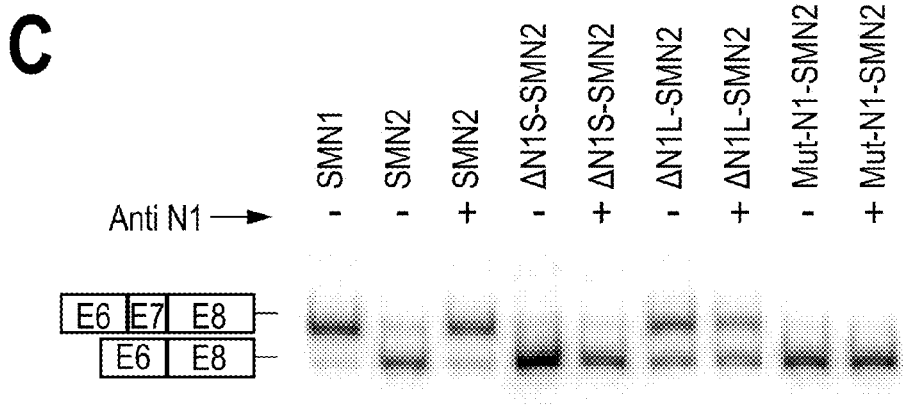

The preceding results further revealed the ISS-N1 negative element located downstream of the U1 snRNA binding site in intron 7 between positions 10 and 24. To confirm that the stimulatory effect of ISS-N1 deletion was not due to the creation of an enhancer element, two additional 20 and 25 nucleotide-long deletions were made. Both deletions included the complete ISS-N1 sequence (mutants N1Δ10-29 and N1Δ10-34, FIG. 4A). Similar to ISS-N1 deletion (mutant N1Δ10-24), they restored exon 7 inclusion in SMN2 to the level of SMN1 (FIG. 4B, lanes 17 and 18). In all three mutants (N1Δ10-24, N1Δ10-29 and N1Δ10-34), the nature of the sequences downstream of the U1 snRNA binding site was different, demonstrating that exon 7 inclusion was not due to the gain of a specific cis-element but due to the loss of ISS-N1.

To determine whether ISS-N1-mediated downregulation of exon 7 inclusion in SMN2 was tissue-specific, five additional cell lines were used that included human neuroblastoma (SK-N-SH), human embryonal kidney cells (HEK 293), mouse neuroblastoma (Neuro-2a), mouse embryonal teratocarcinoma (P19) and mouse motor-neuron-like cells (NSC 34). These cell lines were transfected with ISS-N1-deleted SMN2 minigene (mutant N1Δ10-24 in FIG. 4A; mutant N1Δ10-24 is henceforth termed "SMN2ΔISS-N1"). Similar to the cervical carcinoma cell line C33a (FIG. 4B), all cell types supported exon 7 inclusion in SMN2ΔISS-N1 (FIG. 4C). These results demonstrated that ISS-N-1-mediated suppression of SMN2 exon 7 exclusion was not specific to a particular cell type.

Example 5

Selected ISS-N1 Mutants Improve Presentation of the 5' Splice Site of Exon 7

The predicted RNA structure at the 5' splice site (ss) of SMN2 exon 7 for wild-type, mutant 033 and mutant A54G SMN2 pre-mRNAs is shown in FIG. 6. Numbering of the sequences shown starts from exon 7. Exon 7 sequence is depicted in the large-case letters. Intron 7 sequences are indicated by lower-case letters. Circled letters represent substitution mutations. Stem-loop structure TSL2 (dark shading) was broken by A54G substitution that formed co-axial stacking (light shading). Similar co-axial stacking was maintained in mutant 033 (FIG. 3B, lane 13), a mutant that fully restored exon 7 inclusion. These structural results provided a mechanistic rationale for targeting ISS-N1.

Example 6

Mouse Smn lacks ISS-N1

In contrast to human, the mouse genome has a single Smn gene, which is equivalent to human SMN1. Alignment of human and mouse intron 7 showed three substitutions and three deletions in the ISS-N1 region of mouse intron 7 (FIG. 5A). There are also four additional substitutions in the fifteen-nucleotide-long stretch following ISS-N1. To test whether differences between human and mouse intronic sequences affected splicing of exon 7, the ISS-N1 region of the SMN2 minigene was altered to mouse SMN sequence at the corresponding residues by introducing three substitutions and three deletions (mutant SMN2/MS8, FIG. 5A). This SMN2 mutant fully restored exon 7 inclusion (FIG. 5B, lane 11). To further dissect the role of acquired mutations within ISS-N1, the splicing pattern of SMN2 mutants that incorporated different combinations of deletions and substitutions corresponding to mouse sequences was tested. Consistent with the inhibitory role of acquired mutations, a single A18U substitution in the middle of ISS-N1 increased exon 7 inclusion in SMN2 from ~19% to ~34% (mutant SMN2/MS1, FIG. 5B, lane 4). When A18U was combined with G20A, the exon 7 inclusion increased to ~50% (mutant SMN2/MS4, FIG. 5B, lane 7). A deletion of the three nucleotides from positions 11 to 13 accounted for an increase of ~28% (from 19% to 47%; mutant SMN2/MS6, FIG. 5B, lane 9). When this triple deletion was combined with an adjacent C10U substitution, exon 7 inclusion increased to ~66% (mutant SMN2/MS7, FIG. 5B, lane 10). As a control, substitutions within sequences downstream of ISS-N1 were also made. Contrary to mutations within ISS-N1, the effects of these substitutions on SMN2 splicing were negligible (mutants SMN2/MS3 and SMN2/MSS, FIG. 5B, lanes 6 and 8, respectively). These results were fully consistent with the deletion mutant results that defined the approximate boundary of ISS-N1 within human intron 7 (FIGS. 4A and 4B).

Example 7

Antisense RNA-oligo targeting ISS-N1 promotes exon 7 inclusion in SMN2

Antisense oligonucleotides have traditionally been used to block gene function, e.g., a DNA oligonucleotide anneals to mRNA and mRNA is degraded by an RNase H response (Sazani and Kole, J. Clin. Invest. 112, 481-486). On the contrary, antisense RNA oligonucleotides do not elicit RNase H responses and offer an entirely new set of possibilities in which they could be used to modulate genes without degrading mRNA or pre-mRNA (precursor mRNA, e.g., nuclear, unspliced transcripts; Sazani and Kole, J. Clin. Invest. 112, 481-486; Kole, Oligonucleotides 14, 65-74; Mercatante et al., Curr. Cancer Drug Targets 1, 211-30). RNA antisense oligonucleotides could also be used to test/confirm the presence or absence of a cis-element associated with protein and/or RNA structure. Having identified such an element (ISS-N1) in SMN2 intron 7, it was desired to confirm the inhibitory nature of this element, through use of an antisense oligonucleotide-based approach. A 20 nt long RNA oligonucleotide was synthesized that anneals to ISS-N1 (termed "anti-N1," 5'-AUUCACUUUCAUAAUGCUGG-3', SEQ ID NO: 39, FIG. 7A). This oligonucleotide was 2'-O-methyl modified and additionally possessed a phosphorothioate backbone for greater stability in vivo (refer to Materials and Methods). Such oligonucleotides provide greater antisense effect through enhanced annealing. Modified oligonucleotides are also resistant to ribonucleases (enzymes that degrade RNAs), which are abundantly present in the cell. Different concentrations of antisense oligonucleotides in combination with a fixed concentration of an SMN2 minigene were used to transfect C33a cells (these cells show high transfection efficiency). Lipofectamine™ 2000 reagent (Invitrogen) was used for co-transfection of anti-N1 with the SMN2 minigene. Spliced products were analyzed after 20 hours of transfection. The anti-N1 oligonucleotide produced a dramatic stimulatory effect on inclusion of SMN2 exon 7 in the SMN2 splice product, thereby confirming the inhibitory nature of the ISS-N1 domain that is the target of the anti-N1 oligonucleotide. The stimulatory effect was pronounced even at the lowest concentrations of anti-N1 oligonucleotide (25 nM). Control oligonucleotides that did not anneal to the ISS-N1 site showed no stimulatory effect (FIG. 7B). The effect of anti-N1 oligonucleotide treatment was also observed in a longer SMN2 minigene that contained genomic sequence from exons 4-to-8 (data not shown). These results confirmed the sequence-specific effect of anti-N1 oligonucleotide treatment.

Example 8

The Anti-N1 Oligonucleotide Effect was Specific to the ISS-N1 Target

Figure 8:
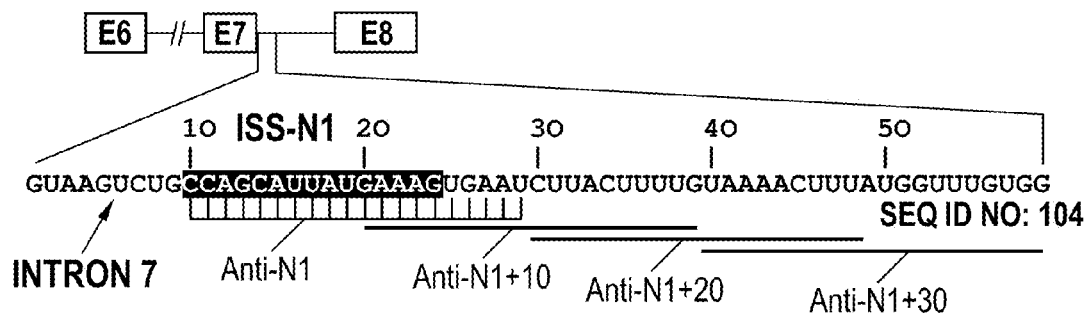
FIGS. 8A-C show the effect of antisense oligonucleotides on splicing of different minigenes.
Figure 8:
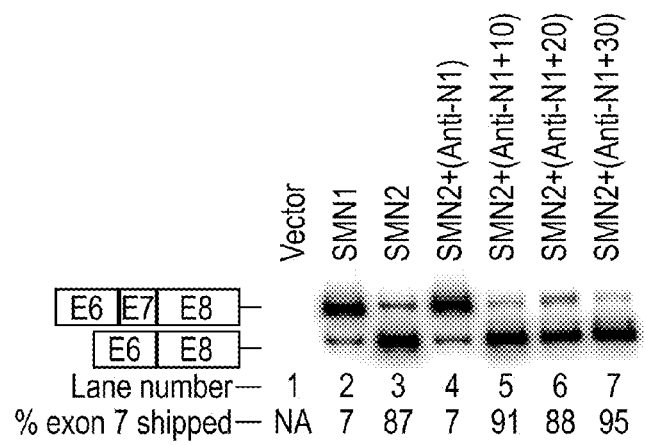
Figure 8:
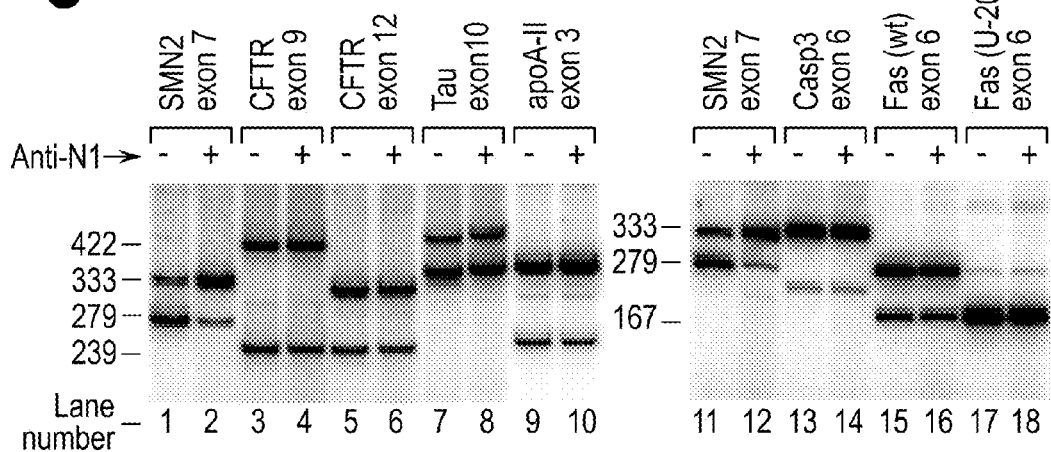

The specificity of the antisense anti-N1 oligonucleotide was initially determined by use of four overlapping antisense RNA-oligonucleotides (anti-N1 and three additional oligonucleotides termed anti-N1+10, anti-N1+20 and anti-N1+30, respectively; FIG. 8A). These antisense oligonucleotides were complementary to intronic sequences downstream of U1 snRNA binding site, including ISS-N1 region were generated. Antisense oligonucleotide Anti-N1 fully blocked ISS-N1 by annealing to a 20-nucleotide-long sequence starting from position 10 of intron 7 (FIG. 8A). Antisense oligonucleotide Anti-N1+10 partially targeted ISS-N1 by annealing to a sequence starting from position 20 of intron 7 (FIG. 8A). Anti-N1+20 and Anti-N1+30 annealed to sequences downstream of ISS-N1 starting from positions 30 and 40, respectively (FIG. 8A). To increase the intracellular stability of these oligonucleotides, each were modified to comprise a phosphorothioate backbone and 2'-O-methyl modification in the sugar moiety. Antisense oligonucleotides with similar modifications have previously been used to correct aberrant splicing in vivo (Crooke, S. T. 2004. *Curr. Mol. Med.* 4:465-487; Lu Q. L., et al. 2005. *Proc. Natl. Acad. Sci. USA* 102: 198-203).

The effect of antisense oligonucleotides on SMN2 splicing was determined by co-transfection of C33a cells with 1.0 μg of SMN2 minigene and 50 nM of antisense oligonucleotides. Consistent with the result obtained for deletion mutant N1Δ10-29 above (FIG. 4B), the Anti-N1 oligonucleotide restored exon 7 inclusion in SMN2 to the level of SMN1 (FIG. 8B, lane 4). The complete restoration of SMN2 exon 7 inclusion was also observed at Anti-N1 concentration as low as 10 nM when the amount of SMN2 minigene was reduced to 0.1 μg (not shown). The three antisense oligonucleotides tested that annealed to intron 7 sequences downstream of ISS-N1 did not produce any stimulatory effect (FIG. 8B, lanes 5-7). The described results were reproducible with two different batches of antisense oligonucleotides synthesized at different times. These results confirmed the sequence-specific effect of antisense oligonucleotide treatment and validated ISS-N1 as the target for antisense-mediated therapy. The splicing effect of anti-ISS-N1 oligonucleotide was additionally observed at all concentrations tested (data not shown).

To confirm that Anti-N1 did not globally impact alternative splicing of other exons, C33a cells were transfected with different minigenes in the presence and absence of Anti-N1, and in vivo splicing patterns were determined. These minigenes were randomly selected and represented a robust mix of exon-including and exon-excluding cassettes (FIG. 8C). Among minigenes that showed low skipping of exons were pTBEx9-V456F (~25% skipping of CFTR exon 9), pTBEx12-50A (~20% skipping of CFTR exon 12), pTBApo-ISE3m (~15% skipping apoA-II exon 3), Casp3 (~6% skipping of Caspase 3 exon 6) and CMV-Fas (wt; ~6% skipping of Fas exon 6). Among minigenes that showed mostly skipping of exons were SI9/LI10 (~85% skipping of Tau exon 10) and CMV-Fas (U-20C; ~98% skipping of Fas exon 6). In the above experiments, 50 nM of Anti-N1 was used, and the minigene-containing plasmid concentration was decreased to 0.1 μg. A high Anti-N1 to minigene ratio was deliberately chosen to detect any non-specific effect of the Anti-N1 oligonucleotide at a non-limiting Anti-N1 concentration. No appreciable change in the splicing pattern of any of the minigenes co-transfected with Anti-N1 was observed (FIG. 8C), demonstrating the specificity of the Anti-N1 splicing effect to SMN intron 7.

Example 9

Figure 9:
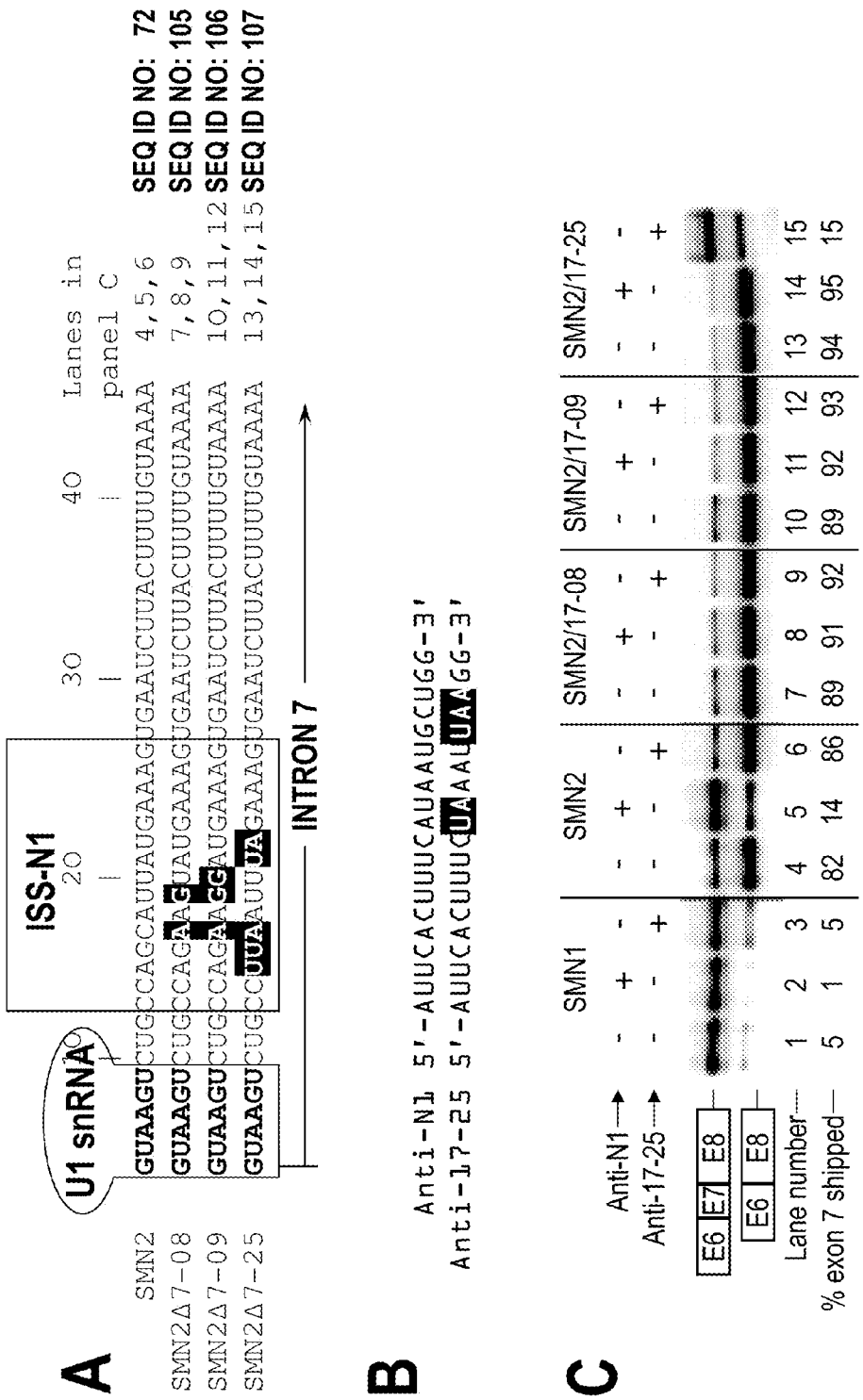
FIGS. 9A-C show the effect of base-pairing between Anti-N1 and ISS-N1 on the efficiency of SMN2 exon 7 inclusion.

Stimulatory Effect of Anti-N1 was Caused by Base Pairing with the Target Sequence To prove that the stimulatory effect of Anti-N1 was solely due to the blocking of ISS-N1, co-transfection experiments were performed with SMN2 minigenes that had random mutations within ISS-N1 (FIG. 9A). Of note, from a large library of ISS-N1 mutants, only those containing substitutions that did not effect SMN2 exon 7 inclusion but that abrogated base pairing between ISS-N1 and Anti-N1 were chosen for testing. Consequently, upon co-transfection, Anti-N1 did not stimulate exon 7 inclusion in any of these mutants (FIG. 9C). Remarkably, the stimulatory effect of Anti-N1 completely disappeared even with a mutant that had only a two base-pair mismatch with Anti-N1 (FIG. 9C, lanes 7, 8). Notably, Anti-N1 also reduced SMN1 exon 7 exclusion from ~5% to ~1% (FIG. 9C, compare lane 1 with lane 2), suggesting that blocking of ISS-N1 had the potential to upregulate SMN expression from both SMN1 and SMN2. To further confirm that the observed antisense-oligonucleotide-mediated stimulatory effect was due to base pairing between the antisense oligonucleotide and ISS-N1, a mutant oligonucleotide was included in these co-transfection experiments (Anti-I7-25, FIGS. 9B and C). This oligonucleotide formed perfect base pairing with the ISS-N1 region of SMN2/17-25 minigene. The SMN2/17-25 construct was chosen for targeting because its ISS-N1 region contains five substitutions (33% change that includes more than two-fold increase in U residues and 33% decrease in G residues in a 15-nucleotide long ISS-N1). Therefore, by using Anti-I7-25, the effect of base pairing could be tested in a mutant that retained inhibitory function despite a major change in the sequence composition. Remarkably, Anti-I7-25 produced about a six-fold increase in exon 7 inclusion in SMN2/17-25 (FIG. 9C, lane 15). At the same time, Anti-I7-25 had no stimulatory effect on the splicing pattern of SMN1 or SMN2 minigenes. Similarly, Anti-I7-25 did not effect the splicing pattern of mutants SMN2/I7-08 and SMN2/I7-09. The above results conclusively confirmed the inhibitory role of ISS-N1 and demonstrated that the antisense oligonucleotides produced a specific stimulatory effect on exon 7 inclusion when ISS-N1 was blocked by base pairing.

Example 10

Figure 10:
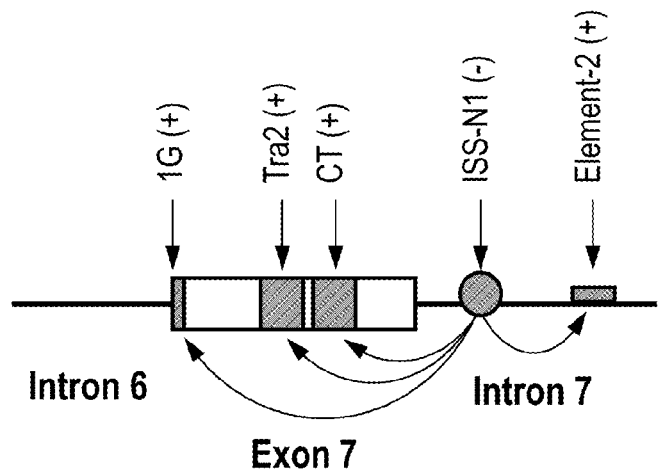
FIGS. 10A and B show the relative significance of exon 7 cis-elements as compared to ISS-N1.
FIG. 10B shows the in vivo splicing pattern of SMN1 mutants, in which deletion of ISS-N1 (combined with abrogation of a given positive cis-element. Spliced products were the same as indicated in FIG. 4B. Abr-E2 represents abrogation of element 2 by a triple substitution G69C/U70A/U71A as in intron 7 (Miyaso, H., et al. 2003. *J. Biol. Chem.* 278:15825-15831), Abr-Tra2 represents abrogation of Tra2-ESE by 25U26U mutation in exon 7 (Hofmann, Y., et al. 2000. *Proc. Natl. Acad. Sci. USA* 97:9618-23), 1U mutation represents abrogation of a cis-element at the first position (Singh, N. N., et al. 2004. *RNA* 10:1291-1305) and Abr-CT represents abrogation of conserved tract by 36U37U mutation in exon 7 (ibid.).
Figure 10:
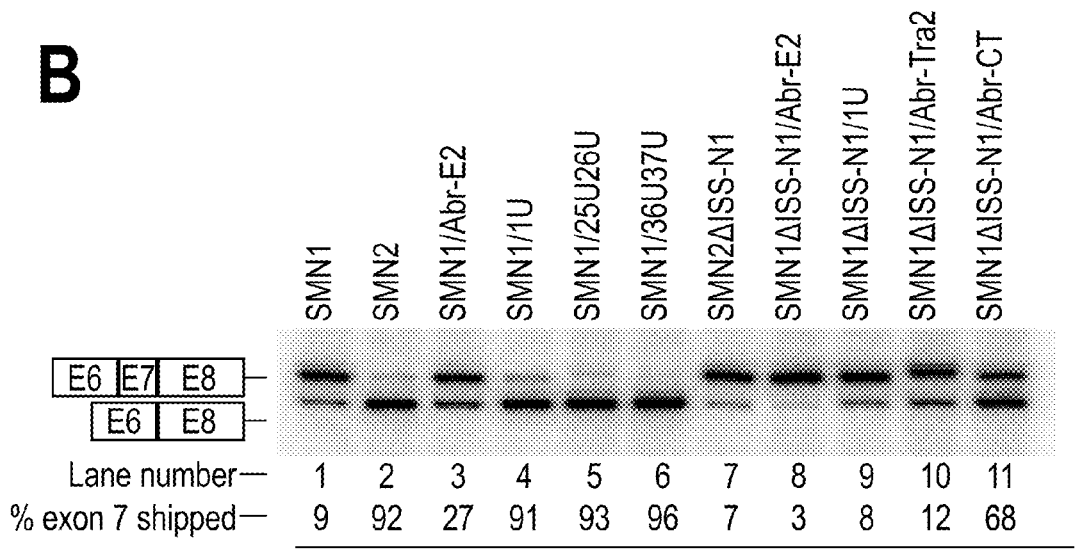

Deletion of ISS-N1 Rescued Exon 7 Inclusion in Mutants with Abrogated Positive cis-Elements To assess the relative impact of ISS-N1 on exon 7 splicing, SMN1 mutants were generated in which ISS-N1 deletion was combined with the abrogation of one of the stimulatory cis-elements. In particular, the impact of ISS-N1 deletion on inhibitory substitutions within four positive cis-elements, i.e., intronic element 2 (Miyajima, H., et al. 2002. *J. Biol. Chem.* 277:23271-23277; Miyaso, H., et al. 2003. *J. Biol. Chem.* 278:15825-15831), Tra2-ESE (Hofmann, Y., et al. 2000. *Proc. Natl. Acad. Sci. USA* 97:9618-23), conserved tract (Singh, N. N., et al. 2004. *RNA* 10:1291-1305) and a critical guanosine residue at the first position of exon 7 (Singh, N. N., et al. 2004. *Biochem. Biophys. Res. Commun.* 315:381-388; Singh, N. N., et al. 2004. *RNA* 10:1291-1305), was tested. The diagrammatic representation of the relative positioning of these elements is shown in FIG. 10A. Demonstrating the cross-exon effect, deletion of ISS-N1 fully restored exon 7 inclusion in SMN1 harboring guanosine-to-uridine substitution at the first position of exon 7 (mutant SMN1ΔISS-N1/ 1U, FIG. 10B, lane 9). Similarly, deletion of ISS-N1 promoted exon 7 inclusion in SMN1 mutants with abrogated element 2 (mutant SMN1ΔISS-N1/Abr-E2, FIG. 10B, lane 8) and abrogated Tra2-ESE (mutant SMN1ΔISS-N1/Abr-Tra2, FIG. 10B, lane 10). Although less prominent, the stimulatory effect of ISS-N1 deletion was clearly detectable in an SMN1 mutant with an abrogated conserved tract (mutant SMN1ΔISS-N1/Abr-CT, FIG. 10B, lane 11). These results demonstrated for the first time that the single, intronic ISS-N1 element had a profound impact on exon 7 splicing in SMN genes.

Example 11

ISS-N1 Showed Portability within SMN2 Intron 7 as well as in a Heterologous System To demonstrate the portability of ISS-N1 within intron 7, four mutants in which ISS-N1 was moved away from the 5' ss of SMN2 exon 7 were generated (FIG. 11A, upper panel). The splicing patterns of these mutants were then tested. While moving ISS-N1 five nucleotides away from its original position fully retained the inhibitory impact of ISS-N1 (FIG. 11B, lane 3), there was a slight decrease in the inhibitory effect (from ~89% to ~72%) when ISS-N1 was displaced an additional five nucleotides (FIG. 11B, lane 4). Moving of ISS-N1 twenty nucleotides away from its original position produced a dramatic effect in which exon 7 exclusion decreased from ~89% to ~18% (FIG. 11B, lane 5). Further displacement of ISS-N1 by another fifteen nucleotides completely eliminated the inhibitory impact of ISS-N1 and restored exon 7 inclusion in SMN2 to the level of SMN1 (FIG. 11B, lane 6). These results demonstrated the limited portability of ISS-N1, as the inhibitory effect of ISS-N1 required close proximity to the 5' ss.

The observation that moving ISS-N1 five nucleotides away from its original position fully retained the inhibitory impact of ISS-N1 (mutant ISS-N-1-M5 in FIG. 11A), suggested that the nature of the five-nucleotide-long sequence UGAAU that immediately preceded ISS-N1 was unable to break the inhibitory context responsible for the ISS-N-1-mediated exclusion of exon 7. To determine whether ISS-N1-associated inhibitory impact was context-specific, the effects of five-nucleotide-long insertions immediately preceding ISS-N1 were examine (FIG. 11A, lower panel). Insertion of five guanosine residues that created an eight-nucleotide-long GC-rich stretch upstream of ISS-N1 did not change exon 7 splicing in SMN2 (FIG. 11B, lane 12). Similarly, insertion of five adenosines upstream of ISS-N1 had negligible effect on splicing pattern of SMN2 (FIG. 11B, lane 9). Insertion of five C residues created a stretch of seven cytosines and partially improved exon 7 inclusion in SMN2 (FIG. 11B, lane 11). However, insertion of five uridines alleviated the inhibitory effect of ISS-N1 and substantially increased SMN2 exon 7 inclusion (FIG. 11B, lane 10). These results showed that the inhibitory impact of ISS-N1 element was not only dependent upon proximity of ISS-N1 to the 5' ss, but was also influenced by the nature of sequences immediately upstream of ISS-N1. As controls, the impacts of identical insertion mutations in SMN1 were tested. These insertions possessed no independent inhibitory effects, as none of these mutations effected SMN1 exon 7 splicing (FIG. 11B, lanes 13-17).

After the limited portability of ISS-N1 within intron 7 of SMN2 was demonstrated, the portability of ISS-N1 in a heterologous context was examined, using a Casp3 minigene that contains Caspase 3 genomic sequence from exon 5 through exon 7. This minigene recapitulated partial skipping of the endogenous Caspase 3 exon 6, as initially reported by Huang et al (Huang, Y., et al. 2001. *Biochem. Biophys. Res. Commun.* 283:762-769). Insertion of an AvrII restriction site downstream of exon 6 did not change the splicing pattern of exon 6 (compare lane 1 in FIG. 11D with lane 13 in FIG. 8C) but enabled insertion of ISS-N1, allowing for testing of the portability of this element in a heterologous context. As shown in FIG. 11C, ISS-N1 sequence was inserted nine nucleotides away from the 5' ss of exon 6 (mutant Casp3ISS-N1, FIG. 11C). This position was selected because ISS-N1 was located at the identical position within intron 7 of SMN genes (FIG. 4A). Interestingly, ISS-N1 insertion caused about a six-fold increase in skipping of Casp3 exon 6 (FIG. 11D, compare lane 1 with lane 3). Blocking of ISS-N1 by a fifteen-nucleotide-long antisense oligo (Anti-ISS-N1/15) fully restored the inclusion of Casp3 exon 6 (FIG. 11D, compare lane 4 with lane 3). The SMN2 minigene was used as the positive control for testing the effect of Anti-ISS-N1/15. As expected, Anti-ISS-N1/15 fully restored exon 7 inclusion in transcripts derived from the SMN2 minigene. The above results confirmed that ISS-N1 was a portable inhibitory element even in a heterologous context. Remarkably, ISS-N1 was able to exert its inhibitory impact despite the presence of G residues at the first and the last position of skipping exon 6 in Casp3 (FIG. 11C). Previously, it has been shown that the presence of a G residue at the last position of exon 7 in SMN2 renders exon 7 exclusion undetectable even in a sensitive radioactive assay (Singh, N. N., et al. 2004. *RNA* 10:1291-1305).

Example 12

Anti-N1 Oligonucleotide Treatment was Effective in SMA type I Fibroblasts

Figure 12:
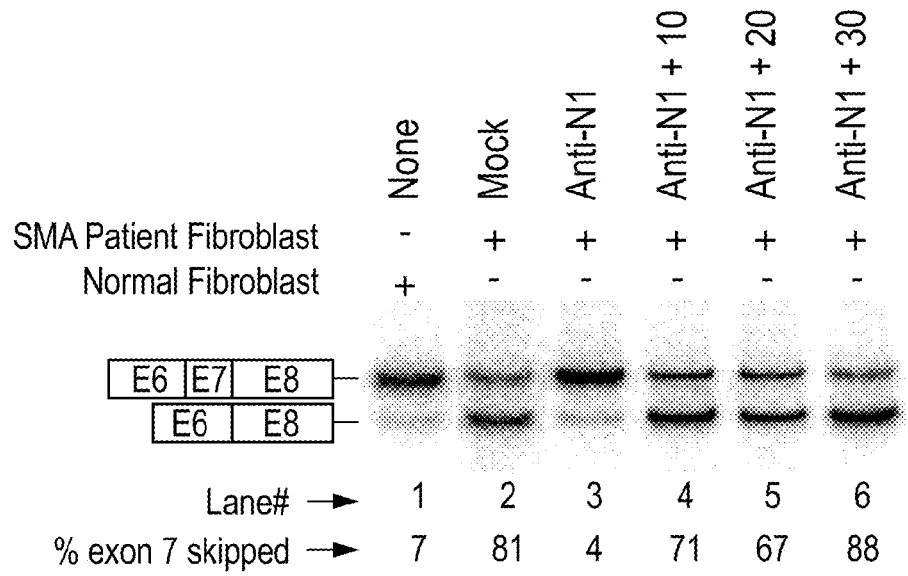
FIGS. 12A-D show the effect of Anti-N1 treatment on the splicing of endogenous genes.
Figure 1:
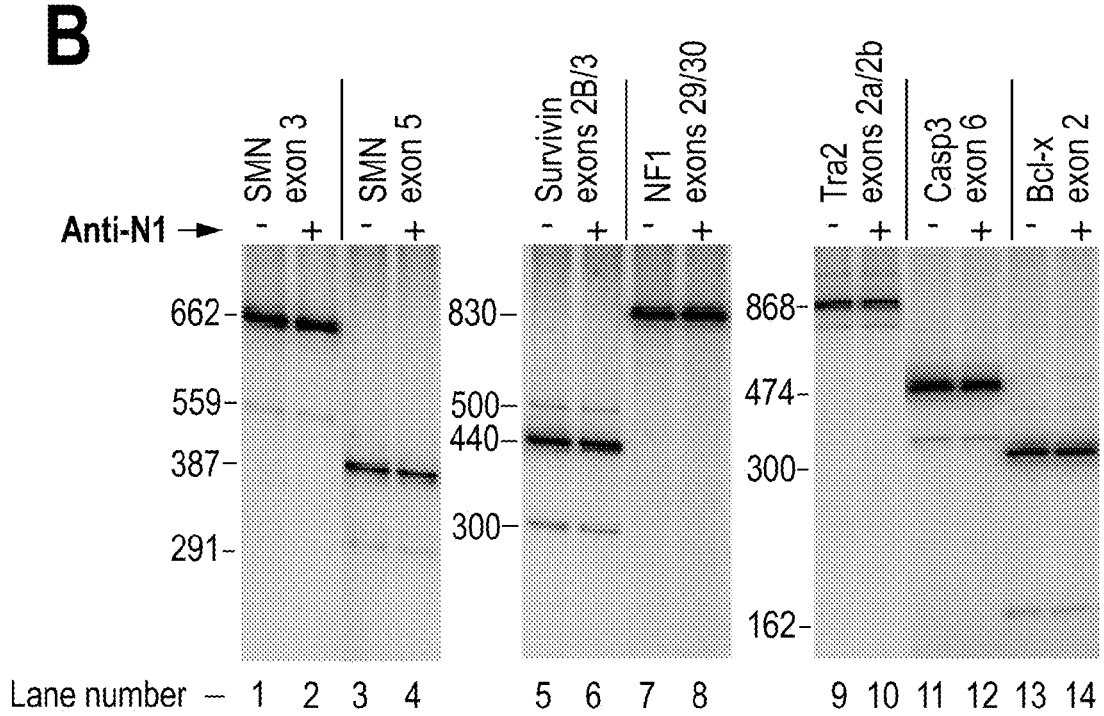
Figure 12:
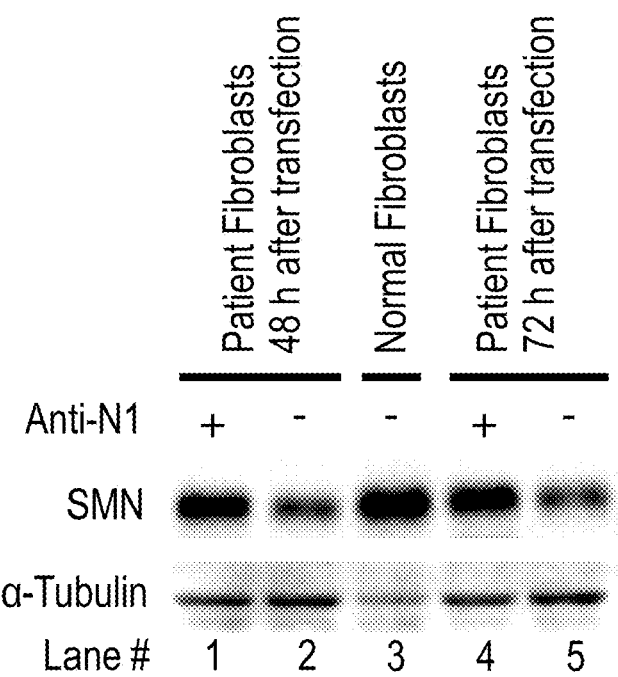
Figure 2:
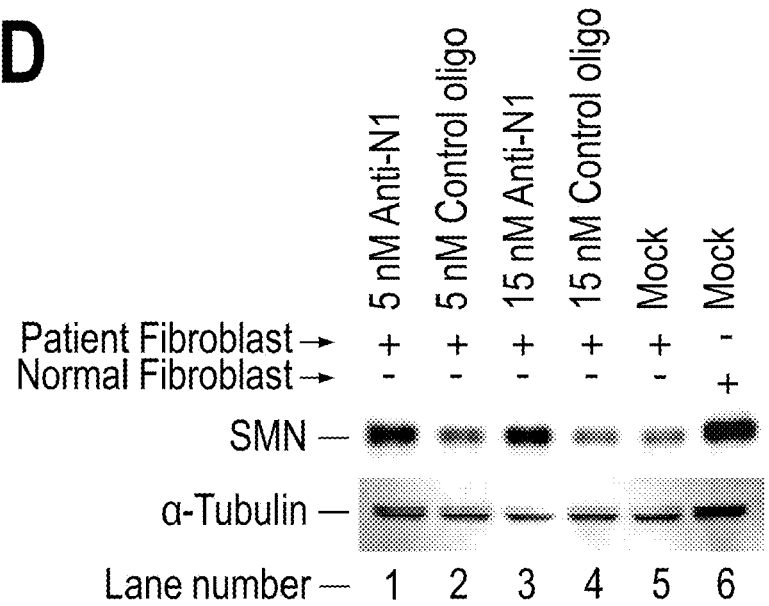

The effect of antisense anti-N1 oligonucleotide treatment in SMA patient cells was examined. Patient-derived SMA type I fibroblasts (specifically, the SMA type I fibroblast line, GM03813, that carries the entire SMN2 gene but no SMN1 gene) were transfected (using Lipofectamine™ 2000 (Invitrogen)) in parallel with antisense oligonucleotides anti-N1, anti-N1+10, anti-N1+20, and anti-N1+30. Due to the absence of SMN1 in GM03813 cells, these cells produced high levels of exon 7-excluded products (FIG. 12A, lane 2). As expected, transfection of GM03813 cells (SMA cells) with increasing concentrations of Anti-N1 yielded increased exon 7 inclusion (not shown). The minimum concentration at which the level of exon 7 inclusion in SMA cells increased to the level observed in normal fibroblasts was 5 nM. Consequently, SMA cells were transfected with 5 nM of antisense oligonucleotides (Anti-N1, Anti-N1+10, Anti-N1+20 and Anti-N1+30). The annealing positions of the preceding oligonucleotides were the same as shown in FIG. 8A. Only Anti-N1 restored exon 7 inclusion in SMA cells to a level comparable to that observed for normal fibroblasts (FIG. 12A). No splicing effect was observed for oligonucleotides anti-N1+10, anti-N1+20, and anti-N1+30 (FIG. 12A). The experiments were reproducible with two batches of oligonucleotides. These results showed that the ISS-N1 target site is accessible in the endogenous SMN2 transcript, which is several-fold bigger than the transcript derived from the SMN2 minigene used in previous examples. Most significantly, these results also confirmed that the anti-N1 oligonucleotide was specific and highly effective against the ISS-N1 target. The fact that anti-N1 oligonucleotide was highly effective at low concentrations indicates that non-specific effects will be decreased upon therapeutic administration and also makes the therapeutic easier to deliver to a patient (e.g., delivery may be made to a patient with efficacy maintained even if only low concentrations reach the target cells of the patient, e.g., the patient's neuronal cells). Thus, the preceding results validated the inhibitory role of ISS-N1 in the context of the endogenous SMN2 transcript.

To confirm that Anti-N1 did not cause aberrant splicing of other exons in patient cells, the following experiment was performed. RNA preparations from untreated fibroblasts and fibroblasts treated with 5 nM of Anti N1 (FIG. 12A, lanes 2 and 3) were used to determine the splicing pattern of a limited number of the randomly selected endogenous genes that are known to generate alternatively spliced products (Chen, X., et al. 2003. *Cell Biol. Int.* 27:491-496; Huang, Y., et al. 2001. *Biochem. Biophys. Res. Commun.* 283:762-769; Mahotka, C., et al. 1999. Cancer Res. 59:6097-6102; Mercatante, D. R., et al. 2002. *J. Biol. Chem.* 277:49374-49382; Park, V. M., et al. 1998. *Hum. Genet.* 103:382-385). No detectable change was observed in the splicing pattern of any of the examined genes, including Tra2, which produces Tra2-β1 (compare 868 base-pair band in lanes 9 and 10 in FIG. 12B; Chen, X., et al. 2003. *Cell Biol. Int.* 27:491-496). Tra2-β1 plays a stimulatory role in SMN2 exon 7 inclusion, but is downregulated in SMA patient cells (Helmken, C., et al. 2003. *Hum. Genet.* 114:11-21). Also, the splicing pattern of SMN exons 3 and 5 remained unaffected in patient cells treated with Anti-N1. These exons were shown to undergo alternative splicing (Hsieh-Li, H. M., et al. 2000. *Nat. Genet.* 24:66-70). Despite the small sample size, these results did not support a global effect of Anti-N1 on the alternative splicing of other genes.

Example 13

Anti-N1 Oligonucleotide-Treated Fibroblasts Expressed Full-Length SMN Protein

Anti-N1-treated fibroblasts were examined for production of SMN protein. Antisense oligonucleotide (anti-N1) treatment was demonstrated to restore levels of SMN protein in SMA patient cells in the following two experiments (FIGS. 12C and D). In the first, SMA fibroblasts were transfected with anti-N1 oligonucleotide and cell lysates were prepared 48 and 72 hours post-transfection. Levels of SMN protein increased in cells treated with anti-N1 as compared to untransfected cells (FIG. 12C). To ensure even protein loading, membranes were stained with Sypro Ruby Protein Blot stain (Bio-Rad). In addition, SMN protein levels were compared to alpha-tubulin levels as an internal control (though elevated alpha-tubulin levels have consistently been observed in patient fibroblasts as compared to normal fibroblasts). In the second experiment, SMA cells were treated with 5 or 15 nM of Anti-N1. These concentrations fell within the lower range of Anti-N1 concentrations that corrected SMN2 splicing in patient cells. Both concentrations caused a significant increase in SMN protein level (FIG. 12D). These were the first reported results in which an antisense-oligonucleotide-assisted increase in the level of SMN protein in patient cells was detected by western blot. This almost certainly occurred due to a more than five-fold increase in exon 7 inclusion from the endogenous SMN2 gene (FIG. 12A). The level of SMN protein remained elevated for five days after transfection. To confirm the specificity of Anti-N1-induced stimulation, a scrambled oligonucleotide was used as a negative control. As shown in FIG. 12D (lanes 2 and 4), this oligonucleotide did not produce any detectable increase in the levels of SMN protein. These results confirmed that antisense targeting of the ISS-N1 site not only caused inclusion of exon 7 in SMN2 mRNA, but also that elevated levels of exon 7-containing SMN2 mRNA directly led to elevated levels of SMN protein in SMA patient cells.

Example 14

Variant Forms of ISS-N1 Sequence Possessing Splice Site Inhibitory Activity

The following variant forms of ISS-N1 seqeunce were tested in the assay described in Example 4:

| Sequence# | Sequence | SEQ ID NO |
|---|---|---|
| N-IN7-0WT: | CCAGCAUUAUGAAAG | 3 |
| N-IN7-001: | CUAGCAACAUGAAAG | 40 |
| N-IN7-002: | ACAGGCCGAUGAAAG | 41 |
| N-IN7-003: | UGAGAACCAUGAAAG | 42 |
| N-IN7-006: | CGAGUUAGAUGAAAG | 43 |
| N-IN7-007: | CCAGGGGAAUGAAAG | 44 |
| N-IN7-008: | CCAGAAGGAUGAAAG | 45 |
| N-IN7-009: | CGAGUCUCAUGAAAG | 46 |
| N-IN7-01A: | CGAGCGGUAUGAAAG | 47 |
| N-IN7-02A: | GGAGCGGUAUGAAAG | 48 |
| N-IN7-20A: | CCAGAGGUAUGAAAG | 49 |
| N-IN7-21A: | CCAGCGGUAUGAAAG | 50 |
| N-IN7-22A: | CCAGCAGUAUGAAAG | 51 |
| N-IN7-008: | CCAGAAGGAUGAAAG | 52 |
| N-IN7-011: | UAAGCCCUAUGAAAG | 53 |
| N-IN7-020: | CUAGUUUUAUGAAAG | 54 |
| N-IN7-025: | CCUUAAUUUAGAAAG | 55 |

Sequence# N-IN7-R1-AA: (SEQ ID NO: 56) AAAGCAUUAUGAAAG

Sequence# N-IN7-R1-UU: (SEQ ID NO: 57) UUAGCAUUAUGAAAG

Sequence# N-IN7-R1-GU: (SEQ ID NO: 58) CGUGCAUUAUGAAAG

Sequence# N-IN7-R3006: (SEQ ID NO: 59) CUGUCAUUAUGAAAG

Sequence# N-IN7-R3C10: (SEQ ID NO: 60) CUUUCAUUAUGAAAG

Sequence# N-IN7-R3C11: (SEQ ID NO: 61) CAUUCAUUAUGAAAG

Sequence# N-IN7-R3B17: (SEQ ID NO: 62) CCAGCAUUAUGAUUA

Sequence# N-IN7-R3A21: (SEQ ID NO: 63) CCAGCAUUAUCUAAG

Sequence# N-IN7-R3C17: (SEQ ID NO: 64) CCAGCAUUAUCCCAG

Sequence# N-IN7-R3A07: (SEQ ID NO: 65) CCAGCAUUAUUUUAG

Sequence# N-IN7-R0709: (SEQ ID NO: 66) CCAGCAUUAAUCAGG

Within the above sequences, underlined nucleotides indicate mutations in the ISS-N1 wild-type sequence. All variant forms above retained the inhibitory function of ISS-N1.

EQUIVALENTS

Those skilled in the art will recognize, or be able to ascertain using no more than routine exper

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, u, unknown, or other

<400> SEQUENCE: 5
ccagcnnnnn gaaag                                                       15

<210> SEQ ID NO 6
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, u, unknown, or other

<400> SEQUENCE: 6
cuuucnnnnn gcugg                                                       15

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcctcgagt ttctaaagaa gatcacagc                                        29

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtcgcggccg caccatcttc tcacttggca t                                     31

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccagcattat gaaag                                                       15

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (1)..(20)
<223> OTHER INFORMATION: O-methyl modified
<220> FEATURE:
<221> NAME/KEY: misc_feature
<222> LOCATION: (1)..(20)
<223> OTHER INFORMATION: phosphorothioate modification of the backbone

<400> SEQUENCE: 10
auucacuuuc auaaugcugg                                               20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: O-methyl modified
<220> FEATURE:
<221> NAME/KEY: misc_feature
<222> LOCATION: (1)..(20)
<223> OTHER INFORMATION: phosphorothioate modification of the backbone

<400> SEQUENCE: 11
caaaaguaag auucacuuuc                                               20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: O-methyl modified
<220> FEATURE:
<221> NAME/KEY: misc_feature
<222> LOCATION: (1)..(20)
<223> OTHER INFORMATION: phosphorothioate modification of the backbone

<400> SEQUENCE: 12
uaaaguuuua caaaaguaag                                               20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: O-methyl modified
<220> FEATURE:
<221> NAME/KEY: misc_feature
<222> LOCATION: (1)..(20)
<223> OTHER INFORMATION: phosphorothioate modification of the backbone

<400> SEQUENCE: 13
ccacaaacca uaaaguuuua                                               20

<210> SEQ ID NO 14
<211> LENGTH: 20
<212> TYPE: RNA
<213> ORGANISM: Artificial Sequence -continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: O-methyl modified
<220> FEATURE:
<221> NAME/KEY: misc_feature
<222> LOCATION: (1)..(20)
<223> OTHER INFORMATION: phosphorothioate modification of the backbone

<400> SEQUENCE: 14
uccuuuaaag uauugugacc                                                  20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: O-methyl modified
<220> FEATURE:
<221> NAME/KEY: misc_feature
<222> LOCATION: (1)..(20)
<223> OTHER INFORMATION: phosphorothioate modification of the backbone

<400> SEQUENCE: 15
auucacuuuc uaaauuaagg                                                  20

<210> SEQ ID NO 16
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: O-methyl modified
<220> FEATURE:
<221> NAME/KEY: misc_feature
<222> LOCATION: (1)..(15)
<223> OTHER INFORMATION: phosphorothioate modification of the backbone

<400> SEQUENCE: 16
cuuucauaau gcugg                                                       15

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagcttgcat cgaatcagta g                                                21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 18
cgactcacta taggctagcc                                                   20

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcatgcaagc ttccttttt ctttcccaac ac                                     32

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caacttcaag ctcctaagcc actgc                                             25

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
taggatccgg tcaccaggaa gttggttaaa tca                                    33

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtgtccact cccagttcaa                                                   20

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccctggttta tgatggatgt tgcctaatga g                                      31

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
```

```
gtcgacgaca cttgctcaac                                              20
```

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
ccagattctc ttgatgatgc tgatgctttg gg                                32
```

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gcatgcaagc ttccttttt ctttcccaac ac                                 32
```

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
cggaattcca atgaaaatga aagccaagtt tcaac                             35
```

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
atagtttagc ggccgccata taatagccag tatgatag                          38
```

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
cggaattcca tggcgatgag cagcggcggc ag                                32
```

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
atagtttagc ggccgccttt cctggtccca gtcttgg                           37
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcatgggtgc cccgacgttg                                           20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctccggcca gaggcctcaa                                           20

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catgagcgac agcggcgagc agaa                                      24

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttaatagcga cgaggtgagt a                                         21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catggcagca gtaaagcaag                                           20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcattgttcc catagagttc c                                         21

<210> SEQ ID NO 37

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggagtacacc aagtatcatg ag                                                  22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cattatgctt gcaaaaacga ac                                                  22

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
auucacuuuc auaaugcugg                                                     20

<210> SEQ ID NO 40
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cuagcaacau gaaag                                                          15

<210> SEQ ID NO 41
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
acaggccgau gaaag                                                          15

<210> SEQ ID NO 42
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ugagaaccau gaaag                                                          15

<210> SEQ ID NO 43
<211> LENGTH: 15
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 43
cgaguuagau gaaag                                                    15

<210> SEQ ID NO 44
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccaggggaau gaaag                                                    15

<210> SEQ ID NO 45
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ccagaaggau gaaag                                                    15

<210> SEQ ID NO 46
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cgagucucau gaaag                                                    15

<210> SEQ ID NO 47
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cgagcgguau gaaag                                                    15

<210> SEQ ID NO 48
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ggagcgguau gaaag                                                    15

<210> SEQ ID NO 49
<211> LENGTH: 15
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 49
ccagagguau gaaag                                                          15

<210> SEQ ID NO 50
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ccagcgguau gaaag                                                          15

<210> SEQ ID NO 51
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ccagcaguau gaaag                                                          15

<210> SEQ ID NO 52
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ccagaaggau gaaag                                                          15

<210> SEQ ID NO 53
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uaagcccuau gaaag                                                          15

<210> SEQ ID NO 54
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cuaguuuuau gaaag                                                          15

<210> SEQ ID NO 55
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 55
ccuuaauuua gaaag                                            15

<210> SEQ ID NO 56
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
aaagcauuau gaaag                                            15

<210> SEQ ID NO 57
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uuagcauuau gaaag                                            15

<210> SEQ ID NO 58
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
cgugcauuau gaaag                                            15

<210> SEQ ID NO 59
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cugucauuau gaaag                                            15

<210> SEQ ID NO 60
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cuuucauuau gaaag                                            15

<210> SEQ ID NO 61
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
```
cauucauuau gaaag 15

<210> SEQ ID NO 62
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ccagcauuau gauua 15

<210> SEQ ID NO 63
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ccagcauuau cuaag 15

<210> SEQ ID NO 64
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ccagcauuau cccag 15

<210> SEQ ID NO 65
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ccagcauuau uuuag 15

<210> SEQ ID NO 66
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ccagcauuaa ucagg 15

<210> SEQ ID NO 67
<211> LENGTH: 80
<212> TYPE: RNA
<213> ORGANISM: Homo sapiens

<400> SEQUENCE: 67
caggguuuag acaaaaucaa aaagaaggaa ggugcucaca uuccuuaaau uaaggaguaa    60
gucugccagc auuaugaaag                                               80

-continued

```
<210> SEQ ID NO 68
<211> LENGTH: 11
<212> TYPE: RNA
<213> ORGANISM: Homo sapiens

<400> SEQUENCE: 68
auacuuaccu g                                                              11

<210> SEQ ID NO 69
<211> LENGTH: 24
<212> TYPE: RNA
<213> ORGANISM: Homo sapiens

<400> SEQUENCE: 69
cuuaaauuaa ggaguaaguc ugcc                                                24

<210> SEQ ID NO 70
<211> LENGTH: 11
<212> TYPE: RNA
<213> ORGANISM: Homo sapiens

<400> SEQUENCE: 70
guaagucugc c                                                              11

<210> SEQ ID NO 71
<211> LENGTH: 23
<212> TYPE: RNA
<213> ORGANISM: Homo sapiens

<400> SEQUENCE: 71
guaagucugc cagcauuaug aaa                                                 23

<210> SEQ ID NO 72
<211> LENGTH: 44
<212> TYPE: RNA
<213> ORGANISM: Homo sapiens

<400> SEQUENCE: 72
guaagucugc cagcauuaug aaagugaauc uuacuuuugu aaaa                          44

<210> SEQ ID NO 73
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
guaagucuga uuaugaaagu gaaucuuacu uuuguaaaa                                39

<210> SEQ ID NO 74
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
guaagucugc cagcgaaagu gaaucuuacu uuuguaaaa                                39

<210> SEQ ID NO 75
<211> LENGTH: 39
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 75
guaagucugc cagcauuauu gaaucuuacu uuuguaaaa                              39

<210> SEQ ID NO 76
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
guaagucugc cagcauuaug aaagcuuacu uuuguaaaa                              39

<210> SEQ ID NO 77
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
guaagucugc cagcauuaug aaagugaauu uuuguaaaa                              39

<210> SEQ ID NO 78
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
guaagucugg aaagugaauc uuacuuuugu aaaa                                   34

<210> SEQ ID NO 79
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
guaagucugc cagcugaauc uuacuuuugu aaaa                                   34

<210> SEQ ID NO 80
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
guaagucugc cagcauuauc uuacuuuugu aaaa                                   34

<210> SEQ ID NO 81
<211> LENGTH: 34
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 81
guaagucugc cagcauuaug aaaguuuugu aaaa                                    34

<210> SEQ ID NO 82
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
guaagucugu gaaucuuacu uuuguaaaa                                          29

<210> SEQ ID NO 83
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
guaagucugc cagccuuacu uuuguaaaa                                          29

<210> SEQ ID NO 84
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
guaagucugc cagcauuauu uuuguaaaa                                          29

<210> SEQ ID NO 85
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
guaagucugc cagcauuaug aaaguaaaa                                          29

<210> SEQ ID NO 86
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
guaagucugc uuacuuuugu aaaa                                               24

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 87
guaagucugu uuuguaaaa                                              19

<210> SEQ ID NO 88
<211> LENGTH: 42
<212> TYPE: RNA
<213> ORGANISM: Homo sapiens

<400> SEQUENCE: 88
guaagucugc cagcauuaug aaagugaauc uuacuuuugu aa                    42

<210> SEQ ID NO 89
<211> LENGTH: 39
<212> TYPE: RNA
<213> ORGANISM: Mus musculus

<400> SEQUENCE: 89
guaagucugu cauuuuaaaa gcuaauuuua ccuuuguaa                        39

<210> SEQ ID NO 90
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
guaagucugc cagcauuuug aaagugaauc uuacuuuugu aa                    42

<210> SEQ ID NO 91
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
guaagucugc cagcauuaua aaagugaauc uuacuuuugu aa                    42

<210> SEQ ID NO 92
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
guaagucugc cagcauuaug aaagugaauc uuaccuuugu aa                    42

<210> SEQ ID NO 93
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
guaagucugc cagcauuuua aaagugaauc uuacuuuugu aa                    42

<210> SEQ ID NO 94
<211> LENGTH: 42
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
guaagucugc cagcauuaug aaagcuaauu uuacuuuugu aa                              42

<210> SEQ ID NO 95
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
guaagucugc cauuaugaaa gugaaucuua cuuuuguaa                                  39

<210> SEQ ID NO 96
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
guaagucugu cauuaugaaa gugaaucuua cuuuuguaa                                  39

<210> SEQ ID NO 97
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
guaagucugu cauuuaaaa gugaaucuua cuuuuguaa                                   39

<210> SEQ ID NO 98
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
guaagucugu cauuuaaaa gcuaauuuua cuuuuguaa                                   39

<210> SEQ ID NO 99
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
guaagucugu cauuuaaaa gcuaauuuua ccuuuguaa                                   39

<210> SEQ ID NO 100
<211> LENGTH: 59
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 100
auuccuuaaa uuaaggggua agucugccag cauuaugaaa gugaaucuua cuuuuguaa         59

<210> SEQ ID NO 101
<211> LENGTH: 59
<212> TYPE: RNA
<213> ORGANISM: Homo sapiens

<400> SEQUENCE: 101
auuccuuaaa uuaaggagua agucugccag cauuaugaaa gugaaucuua cuuuuguaa         59

<210> SEQ ID NO 102
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
auuccuuaaa uuaaggagua agucugcuag agguaugaaa gugaaucuua cuuuuguaa         59

<210> SEQ ID NO 103
<211> LENGTH: 57
<212> TYPE: RNA
<213> ORGANISM: Homo sapiens

<400> SEQUENCE: 103
guaagucugc cagcauuaug aaagugaauc uuacuuuugu aaaacuuuau gguugu            57

<210> SEQ ID NO 104
<211> LENGTH: 59
<212> TYPE: RNA
<213> ORGANISM: Homo sapiens

<400> SEQUENCE: 104
guaagucugc cagcauuaug aaagugaauc uuacuuuugu aaaacuuuau gguugugg          59

<210> SEQ ID NO 105
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
guaagucugc cagaaguaug aaagugaauc uuacuuuugu aaaa                         44

<210> SEQ ID NO 106
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
guaagucugc cagaaggaug aaagugaauc uuacuuuugu aaaa                         44

<210> SEQ ID NO 107
<211> LENGTH: 44
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
guaagucugc cuuaauuuag aaagugaauc uuacuuuugu aaaa                    44

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
auucacuuuc uaaauuaagg                                               20

<210> SEQ ID NO 109
<211> LENGTH: 64
<212> TYPE: RNA
<213> ORGANISM: Homo sapiens

<400> SEQUENCE: 109
guaagucugc cagcauuaug aaagugaauc uuacuuuugu aaaacuuuau gguuugugga   60
aaac                                                                64

<210> SEQ ID NO 110
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
guaagucugu gaauccagca uuaugaaagc uuacuuuugu aaaacuuuau gguuugugga   60
aaac                                                                64

<210> SEQ ID NO 111
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
guaagucugu gaaucuuacc cagcauuaug aaaguuuugu aaaacuuuau gguuugugga   60
aaac                                                                64

<210> SEQ ID NO 112
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
guaagucugu gaaucuuacu uuuguaaaac cagcauuaug aaagcuuuau gguuugugga   60
aaac                                                                64
```

```
<210> SEQ ID NO 113
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
guaagucugu gaaucuuacu uuuguaaaac uuuaugguuu guggccagca uuaugaaaga       60
aaac                                                                   64

<210> SEQ ID NO 114
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
guaagucuga aaaccagca uuaugaaagu gaaucuuacu uuuguaaaa                    49

<210> SEQ ID NO 115
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
guaagucugu uuuccagca uuaugaaagu gaaucuuacu uuuguaaaa                    49

<210> SEQ ID NO 116
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
guaagucugc cccccagca uuaugaaagu gaaucuuacu uuuguaaaa                    49

<210> SEQ ID NO 117
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
guaagucugg ggggccagca uuaugaaagu gaaucuuacu uuuguaaaa                   49

<210> SEQ ID NO 118
<211> LENGTH: 50
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 118
```

```
gccugaccug gugagaacgc cuagguuaca cauaaugaau guuacaugug          50

<210> SEQ ID NO 119
<211> LENGTH: 50
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 119
gccugaccug gugagaacgc cagcauuaug aaagccuagg uuacacauaa          50
```

What is claimed:

1. A method of increasing the level of exon 7-containing SMN2 mRNA in a cell comprising contacting the cell with an oligonucleotide, which oligonucleotide comprises a sequence:
   at least 80% complementary to intron 7 of the SMN2 gene over the entire length of the oligonucleotide and
   at least 85% complementary to the sequence set forth in SEQ ID NO:1 or SEQ ID NO:3;
such that the level of exon 7-containing SMN2 mRNA in the cell is increased.

2. The method of claim 1, wherein the oligonucleotide is 15-40 nucleotides in length and is 100% complementary to intron 7 of the SMN2 gene over the full length of the oligonucleotide.

3. The method of claim 1, wherein the oligonucleotide is complementary to the sequence set forth in SEQ ID NO:1.

4. The method of claim 1, wherein the oligonucleotide is complementary to the sequence set forth in SEQ ID NO:3.

5. The method of claim 1, wherein the oligonucleotide is 15-40 nucleotides in length.

6. The method of claim 1, wherein the oligonucleotide is about 10-15 nucleotides in length.

7. The method of claim 1, wherein the oligonucleotide is about 15-20 nucleotides in length.

8. The method of claim 1, wherein the oligonucleotide comprises at least one modified nucleotide.

9. The method of claim 1, wherein the oligonucleotide comprises at least one modified sugar moiety.

10. The method of claim 1, wherein the oligonucleotide comprises at least one morpholino moiety.

11. The method of claim 1, wherein the oligonucleotide comprises at least one 2'-deoxy ribonucleotide.

12. The method of claim 1, wherein the 2'-deoxy ribonucleotide is 2'-deoxy adenosine or 2'-deoxy guanosine.

13. The method of claim 1, wherein the oligonucleotide comprises at least one modified nucleotide comprising a modified sugar moiety which is modified at the 2'-position.

14. The method of claim 13, wherein the modified sugar moiety comprises a 2-substituent selected from the group consisting of: H, OR, R, halo, SH, SR, $NH_2$, NHR, $NR_2$, and ON, where R is a $C_1$-$C_6$ alkyl, alkenyl, or alkynyl and halo is F, Cl, Br or I.

15. The method of claim 1, wherein the oligonucleotide comprises at least one modified nucleotide selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine.

16. The method of claim 1, wherein the oligonucleotide comprises at least one modified nucleotide selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine.

17. The method of claim 1, wherein the oligonucleotide comprises at least one modified linkage.

18. The method of claim 17, wherein the at least one modified linkage is a phosphorothioate linkage.

19. The method of claim 1, the oligonucleotide comprises at least one locked nucleic acid (LNA) nucleotide.

20. A method of increasing the level of exon 7-containing SMN2 mRNA in an organism, comprising administering to the organism an oligonucleotide, which oligonucleotide comprises a sequence:
   at least 80% complementary to intron 7 of the SMN2 gene over the entire length of the oligonucleotide and
   at least 85% complementary to the sequence set forth in SEQ ID NO:1 or SEQ ID NO:3, such that the level of exon 7-containing SMN2 mRNA in the organism is increased.

21. The method of claim 20, wherein the organism is a mammal.

22. The method of claim 20, wherein the organism is a human.

23. The method of claim 20, wherein the human has spinal muscular atrophy (SMA).

24. A method of treating spinal muscular atrophy (SMA) in a patient, comprising administering to the patient an oligonucleotide, which oligonucleotide comprises a sequence:
   at least 80% complementary to intron 7 of the SMN2 gene over the entire length of the oligonucleotide and
   at least 85% complementary to the sequence set forth in SEQ ID NO:1 or SEQ ID NO:3;
in a dose effective to increase the level of exon 7-containing SMN2 mRNA in cells of the patient, such that SMA in the patient is treated.

25. A method for inhibiting an SMN2 pre-mRNA intronic splicing silencer site in a cell or cell extract comprising contacting the cell with an oligonucleotide 100% complementary to the ISSN-N1 sequence set forth in SEQ ID NO:1, such that the SMN2 intronic splicing silencer site is inhibited.

26. A method for inhibiting an SMN2 pre-mRNA intronic splicing silencer site in an organism comprising administering to the organism an oligonucleotide 100% complementary to the sequence set forth in SEQ ID NO:1, such that the SMN2 intronic splicing silencer site is inhibited.

27. A method of administering an oligonucleotide to a subject comprising comprising administering to a subject an oligonucleotide, which oligonucleotide comprises a sequence:
   at least 80% complementary to intron 7 of the SMN2 gene over the entire length of the oligonucleotide and
   at least 85% complementary to the sequence set forth in SEQ ID NO:1 or SEQ ID NO:3;
wherein the oligonucleotide is administered at a dose effective to increase the level of exon 7-containing SMN2 mRNA in cells of the subject.

28. The method of claim 27, wherein the subject is suffering from amyotrophic lateral sclerosis (ALS).

29. The method of claim 1, wherein the method is performed in vivo.

30. The method of claim 1, wherein the method is performed in vitro.

31. The method of claim 9, wherein the modified sugar moiety comprises a 2'OCH$_3$.

32. The method of claim 17, wherein each linkage of the oligonucleotide is a phosphorothioate linkage.

33. The method of claim 1, wherein the oligonucleotide comprises at least one bicyclic nucleotide.

34. The method of claim 1, wherein each nucleotide of the oligonucleotide is a modified nucleotide.

35. The method of claim 1, wherein each nucleotide of the oligonucleotide comprises a modified sugar moiety.

36. The method of claim 1, wherein each nucleotide of the oligonucleotide is a modified nucleotide and each modified nucleotide comprises the same modification.

37. The method of claim 36, wherein each nucleotide of the oligonucleotide comprises a bicyclic nucleotide.

38. The method of claim 36, wherein each nucleotide of the oligonucleotide comprises a modified sugar moiety which is modified at the 2'-position.

39. The method of claim 38, wherein the modified sugar moiety comprises a 2-substituent selected from the group consisting of: H, OR, R, halo, SH, SR, NH$_2$, NHR, NR$_2$, and ON, where R is a C$_1$-C$_6$ alkyl, alkenyl, or alkynyl and halo is F, Cl, Br or I.

40. The method of claim 38, wherein each modified sugar moiety comprises a 2'OCH$_3$.

41. The method of claim 28, wherein the subject is suffering from spinal muscular atrophy (SMA).

42. The method of claim 30, wherein the cell is selected from the group consisting of a spinal muscular atrophy (SMA) patient-derived neuronal cell, a spinal muscular atrophy (SMA) patient-derived muscle cell or a spinal muscular atrophy (SMA) patient-derived fibroblast.

43. The method of claim 30, wherein the cell is selected from the group consisting of an embryonic stem cell, an embryonic stem cell extract, a neuronal stem cell and a neuronal stem cell extract.

* * * * *